United States Patent [19]

Miranda et al.

[11] Patent Number: 5,958,446
[45] Date of Patent: Sep. 28, 1999

[54] SOLUBILITY PARAMETER BASED DRUG DELIVERY SYSTEM AND METHOD FOR ALTERING DRUG SATURATION CONCENTRATION

[75] Inventors: Jesus Miranda; Steven Sablotsky, both of Miami, Fla.

[73] Assignee: Noven Pharmaceuticals, Inc., Miami, Fla.

[*] Notice: This patent is subject to a terminal disclaimer.

[21] Appl. No.: 08/433,754

[22] Filed: May 4, 1995

Related U.S. Application Data

[62] Continuation of application No. 07/722,342, Jun. 27, 1991, Pat. No. 5,474,783, which is a continuation-in-part of application No. 07/671,709, filed as application No. PCT/US90/01750, Mar. 28, 1990, Pat. No. 5,300,291, which is a continuation-in-part of application No. 07/295,847, Jan. 11, 1989, Pat. No. 4,994,267, which is a continuation-in-part of application No. 07/164,482, Mar. 4, 1988, Pat. No. 4,814,168.

[51] Int. Cl.⁶ ........................................ A61F 13/02
[52] U.S. Cl. .......................... 424/448; 426/449
[58] Field of Search ..................... 424/448, 449

[56] References Cited

U.S. PATENT DOCUMENTS

| | | | |
|---|---|---|---|
| 3,469,308 | 9/1969 | Penneck | 524/506 |
| 4,390,520 | 6/1983 | Nagai et al. | |
| 4,668,232 | 5/1987 | Cordes et al. | 604/897 |
| 4,690,683 | 9/1987 | Chien et al. | 424/448 |
| 4,693,887 | 9/1987 | Shah | |
| 4,814,168 | 3/1989 | Sablotsky et al. | 424/78 |
| 4,845,081 | 7/1989 | Sloan | |
| 4,883,669 | 11/1989 | Chien et al. | |
| 4,906,169 | 3/1990 | Chien et al. | |
| 4,911,916 | 3/1990 | Cleary | |
| 4,931,281 | 6/1990 | Kim et al. | |
| 4,987,893 | 1/1991 | Salamone et al. | |
| 4,994,267 | 2/1991 | Sablotsky | 424/78 |
| 5,032,403 | 7/1991 | Sinreich | 424/448 |
| 5,128,138 | 7/1992 | Blank | 424/449 |
| 5,149,538 | 9/1992 | Granger et al. | 424/499 |
| 5,154,271 | 10/1992 | Otsuka et al. | 424/448 |
| 5,154,922 | 10/1992 | Govil et al. | 424/448 |
| 5,230,898 | 7/1993 | Horstmann et al. | 424/449 |
| 5,252,334 | 10/1993 | Chiang et al. | 424/448 |
| 5,262,165 | 11/1993 | Govil et al. | 424/448 |
| 5,300,291 | 4/1994 | Sablotsky et al. | 424/78.18 |
| 5,336,210 | 8/1994 | Hidaka et al. | 604/307 |
| 5,393,529 | 2/1995 | Hoffmann et al. | 424/445 |
| 5,474,783 | 12/1995 | Miranda et al. | 424/448 |

FOREIGN PATENT DOCUMENTS

| | | |
|---|---|---|
| 0 312 265 | 4/1989 | European Pat. Off. . |
| 0 343 807 | 11/1989 | European Pat. Off. . |
| 0 371 496 | 11/1989 | European Pat. Off. . |
| 0416842 | 3/1991 | European Pat. Off. . |
| 2 105 990 | 4/1993 | United Kingdom . |
| 87/03477 | 6/1987 | WIPO . |

OTHER PUBLICATIONS

Vaughn, "Using Solubility Parameters in Cosmetics Formulation", 36 J. Soc. 319–333 Sep./Oct. 1985.

Pfister et al., "Permeation Enhancers Compatible with Transdermal Drug Delivery Systems Part I: Selection and Formulation Considerations", Medical Device Technology, Sep./Oct. 1990, 48–56.

Sloan et al., "Use of Solubility Parameters of Drug and Vehicle to Predict Flux Through Skin", 87 The Journal of Investigative Dermatology, Aug. 1986, pp. 244–252.

Ulman et al., "Drug Permeability of Modified Silicone Polymers", Journal of Controlled Release, 10 (1989) pp. 273–281.

(Abstract) "Development And Characterization of Pseudolatex Based Transdermal Drug Delivery System of Diclofenac", vol. 17, No. 8, pp. 1041–1058, May 1991.

Yu et al., "Transdermal Dual–Controlled Delivery of Testosterone And Estradiol: (1) Impact of System Design", Drug Devel. Indust. Pharm. 17(14): 1883–1904 (1991).

Lichtenberger et al. "Polymer Films From Aqueous Latex Dispersions As Carriers For Transdermal Delivery of Lipophilic Drugs", Proceed. Intern. Symp. Control. Rel Bioact. Mater., 15, (1988) pp. 147–150.

Pfister & Hseih, "Permeation Enhancers Compatible With Transdermal Drug Delivery Systems Part II: System Design Considerations", Medical Device Technology, pp. 54–60, Oct. 1990.

Peck et al. "Aqueous Dispersions of Water–Soluble and Water–Insoluble Cellulosic Polymers As Vehicles For Topical Drug Delivery", Proceed. Intern. Symp. Control. Rel Bioact., 15, No. 90 (1988) pp. 149–150.

*Primary Examiner*—Jyothsna Venkat
*Attorney, Agent, or Firm*—Foley & Lardner

[57] ABSTRACT

The method of adjusting the saturation concentration of a drug in a transdermal composition for application to the dermis, which comprises mixing polymers having differing solubility parameters, so as to modulate the delivery of the drug. This results in the ability to achieve a predetermined permeation rate of the drug into and through the dermis. In one embodiment, a dermal composition of the present invention comprises a drug, an acrylate polymer, and a polysiloxane. The dermal compositions can be produced by a variety of methods known in the preparation of drug-containing adhesive preparations, including the mixing of the polymers, drug, and additional ingredients in solution, followed by removal of the processing solvents. The method and composition of this invention permit selectable loading of the drug into the dermal formulation and adjustment of the delivery rate of the drug from the composition through the dermis, while maintaining acceptable shear, tack, and peel adhesive properties.

75 Claims, 8 Drawing Sheets

SOLUBILITY PARAMETER BASED DRUG DELIVERY SYSTEM AND METHOD FOR ALTERING DRUG SATURATION CONCENTRATION

CROSS-REFERENCE TO RELATED APPLICATIONS

This application is a continuation of application Ser. No. 07/722,342, filed Jun. 27, 1991, now U.S. Pat. No. 5,474,783, which, is a continuation-in-part of Ser. No. 671,709 now U.S. Pat. No. 5,300,291 on April 2, 1991; which was filed as PCT/US90/01750 on Mar. 28, 1990 which is a continuation-in-part of U.S. patent application Ser. No. 295,847, filed Jan. 11, 1989, now U.S. Pat. No. 4,994,267 issued on Feb. 19, 1991; which is a continuation-in-part of U.S. patent application Ser. No. 164,482, filed Mar. 4, 1988, now U.S. Pat. No. 4,814,168, granted Mar. 21, 1989, which application Ser. No. 164,482 is incorporated herein by reference. All applications and patents are assigned to Noven Pharmaceuticals, Inc. of Miami, Fla.

BACKGROUND OF THE INVENTION

This invention relates generally to transdermal drug delivery systems, and more particularly, to a transdermal drug delivery composition wherein a blend of polymers is utilized to affect the rate of drug delivery from the composition. More specifically, a plurality of polymers having differing solubility parameters, preferably immiscible with each other, adjusts the solubility of the drug in a polymeric adhesive system formed by the blend and modulates the delivery of the drug from the composition and through the dermis.

The use of a transdermal composition, for example a pressure-sensitive adhesive containing a medicament, namely, a drug, as a means of controlling drug delivery through the skin at essentially a constant rate, is well known. Such known delivery systems involve incorporation of a medicament into a carrier such as a polymeric matrix and/or a pressure-sensitive adhesive formulation. The pressure-sensitive adhesive must adhere effectively to the skin and permit migration of the medicament from the carrier through the skin and into the bloodstream of the patient.

Many factors influence the design and performance of sustained or controlled release drug delivery products, and dermal delivery systems in general, including drug properties, optimum delivery rate, target site(s), type of therapy (short-term or chronic), patient compliance, etc. Among the drug properties which are known to influence the rate of release or permeation, or both, into the skin are the physicochemical properties, including molecular size, shape, and volume; solubility (both in the delivery system and through the skin); partitioning characteristics; degree of ionization; charge; and protein binding propensity.

When a drug is contained in a carrier, for example, a pressure-sensitive adhesive for transdermal delivery, the rate of administration may be affected by the rate of release of the drug from the carrier, as well as the rate of passage of the drug through the skin. These rates vary from drug-to-drug and from carrier-to-carrier. A variety of mathematical equations have been proposed in the prior art to describe theoretically the fundamentals of mass transfer phenomena involved in diffusion through a carrier and development of a flux across a membrane such as the skin.

Transdermal drug delivery systems can be divided into two general groups: system-controlled and skin-controlled devices. With skin-controlled devices, net drug delivery is controlled by the rate of drug permeation through the skin. Skin-controlled systems can be further subdivided into monolithic devices and reservoir devices.

Generally, a monolithic system comprises a drug dispersed or dissolved in a matrix comprising a homogeneous polymeric material of, illustratively, silicone adhesive, silicone rubber, acrylic adhesive, polyethylene, polyisobutylene, polyvinyl chloride, nylon, or the like. The drug is dissolved in the polymeric matrix until its saturation concentration is reached. Any additional drug, remains dispersed within the matrix. As drug is removed from the surface of the matrix, more of the drug diffuses out of the interior in response to the decreased concentration at the surface. The release rate is therefore not constant over time, but instead gradually decreases as the drug concentration decreases.

The flux, or percutaneous absorption rate of drugs through the skin, is described by Fick's first law of diffusion:

$$J = -D(dC_m/dx),$$

where J is the flux in $g/cm^2/sec$, D is the diffusion coefficient of the drug through the skin in $cm^2/sec$, and $dC_m/dx$ is the concentration gradient of active agent across the skin.

In order to modify the rate of delivery from a monolithic transdermal device and into the dermis, the prior art has typically focused on selecting a specific single-polymer matrix or a blend of soluble (miscible) polymers. Illustrative examples are the novel polymers described in U.S. Pat. Nos. 4,898,920 and 4,751,087. There is a need in the art to modify the rate of delivery while using commercially available polymer components.

Another common technique for modifying the rate of drug delivery is the addition of a vehicle or enhancer to the formulation to increase the solubility of the drug within the polymer matrix, such as by adding a co-solvent such as a polyhydric alcohol or by changing the skin permeability, such as by adding enhancers such as ethanol. There is a further need to be able to modulate the delivery of a drug from a polymer matrix without adding vehicles or enhancers.

There is no example in the prior art of using a simple blend of adhesive polymers to affect the rate of drug delivery from a monolithic adhesive-based transdermal composition. However, U.S. Pat. No. 4,814,168 granted Mar. 21, 1989 and a continuation-in-part thereof, U.S. Pat. No. 4,994,267 issued on Feb. 19, 1991, both assigned to Noven Pharmaceuticals, Inc., Miami, Fla., disclose the use of a multipolymer, specifically an ethylene/vinyl acetate copolymer or an ethylene/vinyl acetate/acrylic terpolymer, a rubber and a tackifier in a carrier composition to improve the adhesive properties. The composition of U.S. Pat. No. 4,994,267 further includes an acrylate polymer in the system for additional improvement to the adhesive properties.

Drug concentration in a monolithic transdermal delivery device can vary widely depending on the drug and polymers used. For example, certain drugs are effective in low doses and therefore the transdermal formulation may involve low concentrations, illustratively, 5% or less by weight of the medicament in an adhesive. Other drugs, such as nitroglycerin, require large doses to be effective and the transdermal formulation therefore, may involve high drug concentrations, approximately between 5 to 40% or more by weight in an adhesive. Low concentrations of medicament typically do not critically affect the adhesion, tack, and shear resistance properties of the adhesive. However, low drug concentrations in the adhesive can result in difficulties in achieving an acceptable delivery rate of the medicament. High concentrations, on the other hand, frequently affect the adhesion properties of the adhesives. The deleterious effects are particularly exacerbated by drugs which also act as plasticizers, or solvents, for the polymeric adhesive material (e.g., nitroglycerin in polyacrylates).

There is a need in the art for an adhesive composition for transdermal delivery systems which can selectably incorporate low concentrations of drug and deliver same at an adequate and controlled rate or incorporate high concentrations of drugs while retaining good physical adhesive properties.

It is, therefore, an object of this invention to provide a transdermal drug delivery system wherein the rate of drug delivery from the transdermal composition may be selectably modulated.

It is another object of this invention to provide a transdermal drug delivery system wherein the rate of drug delivery from the transdermal composition may be selectably modulated by adjusting the solubility and/or diffusivity of the drug in the multiple polymer adhesive system.

It is also an object of this invention to provide a transdermal drug delivery system wherein the multiple polymer adhesive system is simple to manufacture.

It is a further object of this invention to provide a transdermal drug delivery system wherein drug-loading of a multiple polymer adhesive system may be selectably varied without adverse effects on drug delivery rate and adhesive properties, such as adhesion, tack, and shear resistance.

It is additionally an object of this invention to provide a transdermal drug delivery system wherein a novel multiple polymer adhesive system is provided which has desirable physical properties.

SUMMARY OF THE INVENTION

The foregoing and other objects are achieved by this invention which provides a transdermal drug delivery system wherein a blend of at least two polymers having differing solubility parameters adjusts the solubility of a drug in the polymeric blend and thereby modulates the delivery of the drug from the system and through the dermis.

In accordance with a composition aspect of the invention, an improved pressure-sensitive adhesive composition of the type which is suitable as a matrix for controlled release of a bioactive agent therefrom comprises a blend of a first polymeric adhesive material having a first solubility parameter and a second polymeric adhesive material having a second solubility parameter, the first and second solubility parameters being different from one another. The blend, therefore, has a characteristic net solubility parameter. In embodiments incorporating a bioactive agent in the improved pressure-sensitive adhesive composition, the characteristic net solubility parameter can be preselected to adjust the saturation concentration of a bioactive agent in the composition and thereby control the release of the bioactive agent. The saturation concentration of the bioactive agent may be adjusted either upward or downward depending upon whether the rate of release is to be enhanced or retarded.

In preferred embodiments, the bioactive agent may comprise a drug. In particularly, preferred embodiments, the drug is a steroid, such as an estrogen or a progestational agent, or combination thereof. In other preferred embodiments, the drug may be a $\beta_2$-adrenergic agonist, such as albuterol, or a cardioactive agent, such as nitroglycerin. In still other embodiments, the bioactive agent is a cholinergic agent, such as pilocarpine, or an antipsychotic such as haloperidol or a tranquilizer/sedative such as alprazolam.

The pressure-sensitive adhesive composition may further include enhancers, fillers, co-solvents, and excipients as are known in the art for use in such compositions.

In a preferred embodiment of the improved pressure-sensitive adhesive, the first polymeric adhesive material is a polyacrylate and the second adhesive material is a polysiloxane. The polyacrylate is preferably present in the pressure-sensitive adhesive composition in an amount ranging from about 2–96% by weight and the polysiloxane is present in an amount ranging from about 98–4%. Preferably, the ratio of polyacrylate to polysiloxane is from about 2:98 to about 96:4, and more preferably from about 2:98 to about 86:14 by weight.

In a dermal adhesive composition embodiment of the invention, a multiple polymer adhesive system consists essentially of a blend of 2–96% by weight of an acrylate polymer and 98–4% by weight of a polymer of siloxane, the multiple polymer adhesive system being in an amount of about 99–50% by weight of the dermal adhesive composition. This is combined with a bioactive agent in the amount of 0.3–50% by weight of the total dermal adhesive composition. Optional additives, such as co-solvent for the bioactive agent (up to 30% by weight) and enhancers (up to 20% by weight) may be included in the dermal adhesive composition.

In a transdermal drug delivery device embodiment, the improved pressure-sensitive adhesive of the present invention is combined with a drug. The transdermal drug delivery device may comprise a monolithic adhesive matrix device in some embodiments. Of course, the transdermal drug delivery device may include a backing material and a release liner as is known in the art.

The saturation concentration of a drug in a transdermal drug delivery device of the type having a drug-containing pressure-sensitive adhesive diffusion matrix is adjusted in accordance with a method aspect of the present invention by blending at least two polymers having differing solubility parameters to form a pressure-sensitive adhesive diffusion matrix having a net solubility parameter which modifies the delivery rate of the drug from the pressure-sensitive adhesive diffusion matrix and through the dermis.

BRIEF DESCRIPTION OF THE DRAWING

Comprehension of the invention is facilitated by reading the following detailed description, in conjunction with the annexed drawing, in which.

$$SP_{net} = \Phi_{ps}SP_{ps} + \Phi_{pa}SP_{pa},$$

Figure 15:
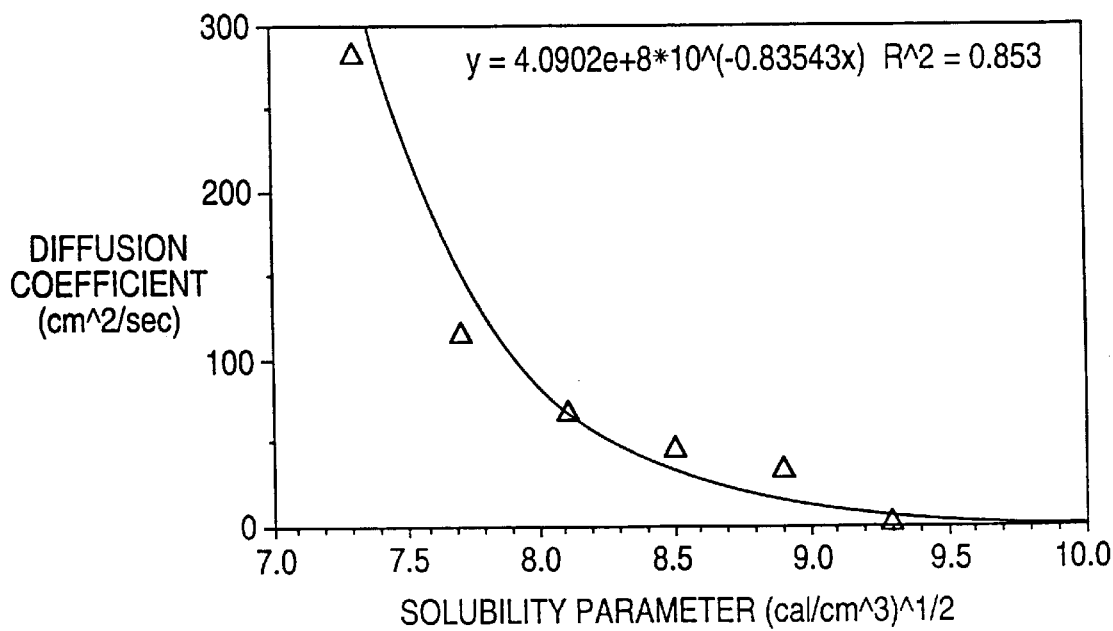

where $\Phi_{ps}$ is the weight percentage of polysiloxane and $SP_{ps}$ is the solubility parameter of polysiloxane. The subscript "pa" refers to the polyacrylate; and FIG. 15 is a plot of diffusion coefficient versus net solubility parameter.

DETAILED DESCRIPTION

In one aspect of the present invention, a pressure-sensitive adhesive composition is provided which consists of a blend of at least two polymers. The blend of at least two polymers is herein referred to as a multiple polymer adhesive system.

The term "blend" is used herein to mean that there is no, or substantially no, chemical reaction or cross-linking (other than simple H-bonding) between the polymers in the multiple polymer adhesive system.

In another aspect of the invention, a controlled release dermal composition comprises a drug, or other bioactive agent, in combination with the multiple polymer adhesive system. In this aspect, the multiple polymer adhesive not only functions as a carrier matrix for the drug, but enhances the rate of release of the drug, and hence the transdermal permeation rate. In some embodiments of the invention, however, the multiple polymer adhesive system will function to retard the transdermal permeation rate.

The invention is premised on the discovery that the transdermal permeation rate of a drug from the multiple polymer adhesive system can be selectively modulated by adjusting the solubility of the drug in the device. As used herein, the term "transdermal permeation rate" means the rate of passage of the drug through the skin; which, as known in the art, may or may not be affected by the rate of release of the drug from the carrier.

The polymers comprising the multiple polymer adhesive system are inert to the drug, and are preferably immiscible with each other. Forming a blend of multiple polymers results in an adhesive system having a characteristic "net solubility parameter," the selection of which advantageously permits a selectable modulation of the delivery rate of the drug by adjusting the solubility of the drug in the multiple polymer adhesive system.

Solubility parameter, also referred to herein as "SP", has been defined as the sum of all the intermolecular attractive forces, which are empirically related to the extent of mutual solubility of many chemical species. A general discussion of solubility parameters is found in an article by Vaughan, "Using Solubility Parameters in Cosmetics Formulation," *J. Soc. Cosmet. Chem.*, Vol.36, pages 319–333 (1985). Many methods have been developed for the determination of solubility parameters, ranging from theoretical calculations to totally empirical correlations. The most convenient method is Hildebrand's method, which computes the solubility parameter from molecular weight, boiling point and density data, which are commonly available for many materials and which yields values which are usually within the range of other methods of calculation:

$$SP = (\Delta E_v/V)^{1/2},$$

where V=molecular weight/density and $\Delta E_v$=energy of vaporization.

Alternatively written, $$SP = (\Delta H_v/V - RT/V)^{1/2}$$

where $\Delta H_v$=heat of vaporization, R=gas constant, and T is the absolute temperature, °K. For materials, such as high molecular weight polymers, which have vapor pressures too low to detect, and thus for which $\Delta H_v$ is not available, several methods have been developed which use the summation of atomic and group contributions to $\Delta H_v$.

$$\Delta H_v = \Sigma_i \Delta h_i,$$

where $\Delta h_i$ is the contribution of the ith atom or group to the molar heat of vaporization. One convenient method has been proposed by R. F. Fedors, *Polymer Engineering and Science*, Vol. 14, p. 147 (1974). In this method $\Delta E_v$ and V are be obtained by simply assuming that $\Delta E_v = \Sigma_i \Delta e_i$ and $V = \Sigma_i v_i$, where $\Delta e_i$ and $v_i$ are the additive atomic and group contributions for the energy of vaporization and molar volume, respectively.

Yet another method of calculating the solubility parameter of a material is described by Small, *J. Applied Chem.* Vol. 3, p. 71 (1953).

Table IA below sets forth solubility parameters of some exemplary adhesive polymers which would be useful in the practice of the invention. Table IA is in $(cal/cm^3)^{1/2}$ and $(J/cm^3)^{1/2}$ as calculated by Small's method.

TABLE IA

| Polymers | Solubility Parameter | |
| --- | --- | --- |
| Addition polymers of unsaturated esters | $(cal/cm^3)^{1/2}$ | $(J/cm^3)^{1/2}$ |
| Polymethyl methacrylate | 9.3 | 19.0 |
| Polyethylmethacrylate | 9.1 | 18.6 |
| Polymethylacrylate | 9.7 | 19.8 |
| Polyethylacrylate | 9.2 | 18.8 |
| Hydrocarbon polymers | | |
| Polyethylene | 8.1 | 16.6 |
| Polystyrene | 9.1 | 18.6 |
| Polyisobutylene | 7.7 | 15.7 |
| Polyisoprene | 8.1 | 16.6 |
| Polybutadiene | 8.4 | 16.6 |
| Polyethylene/butylene | 7.9 | 16.2 |
| Halogen-containing polymers | | |
| Polytetrafluoroethylene | 6.2 | 12.7 |
| Polyvinylchloride | 9.5 | 19.4 |
| Polyvinylidene chloride | 12.2 | 24.9 |
| Polychloroprene | 9.4 | 19.2 |
| Polyacrylonitrile | 12.7 | 26.0 |
| Condensation polymers | | |
| Nylon –6.6 | 13.6 | 27.8 |
| Epon resin 1004 (epoxy) | 9.7 | 19.8 |
| Polysiloxanes | | |
| Polydimethylsiloxane | 7.3 | 14.9 |
| Copolymers | | |
| Polybutadiene-co-acrylonitrile: 75/25 to 70/30 | 9.25 | 18.9 |
| Polybutadiene-co-styrene: 75/25 to 72/28 | 8.5 | 17.4 | excerpted from Kraton ® Thermoplastic Rubber Shell Chemical Co. Product Brochure Number SC: 198-89

Table IB below sets forth solubility parameters calculated by Fedors' method and are expressed in units of $(J/cm^3)^{1/2}$.

TABLE IB

| Components | Solubility Parameter, $(J/cm^3)^{1/2}$ |
| --- | --- |
| polyethylene/vinyl acetate (40% VAc) | 20.9 |
| polydimethylsiloxane | 15.1 |
| polyisobutylene | 17.6 |
| polyethylene | 17.6 |
| polyethylene ethacrylate | 19.8 |
| polyethyl acrylate | 20.9 |
| polymethyl acrylate | 21.7 |
| polymethyl methacrylate | 22.3 |
| polystyrene | 22.5 |
| nitroglycerin | 27.0 |
| estradiol | 24.5 |
| norethindrone acetate | 21.3 |
| pilocarpine | 22.9 |
| albuterol | 26.7 |

In accordance with the principles of the invention, the transdermal permeation rate is controlled by varying the polymer components of the multiple polymer adhesive system so as to alter the difference in the solubility parameter of the multiple polymer adhesive system relative to that of the drug (see, Examples 2–5, or 28 and 29, hereinbelow). Preferably the solubility parameters of the polymer components are different from one other by an increment of at least 2 $(J/cm^3)^{1/2}$. Most preferably, they differ by at least 4 $(J/cm^3)^{1/2}$.

The transdermal permeation rate is also controlled by varying the relative proportions of the polymers comprising the multiple polymer adhesive system (see, Example 6 hereinbelow).

The multiple polymer adhesive system is preferably formulated so that it is a pressure-sensitive adhesive at room temperature and has other desirable characteristics for adhesives used in the transdermal drug delivery art; such characteristics include good adherence to skin, ability to be peeled or otherwise removed without substantial trauma to the skin, retention of tack with aging, etc. In general, the multiple polymer adhesive system should have a glass transition temperature (Tg), measured using a differential scanning calorimeter, of between about –70 C. and 0° C.

Selection of the particular polymer composition is governed in large part by the drug to be incorporated in the device, as well as the desired rate of delivery of the drug. Those skilled in the art can readily determine the rate of delivery of drugs from the multiple polymer transdermal adhesive system in order to select suitable combinations of polymers and drug for a particular application. Various techniques can be used to determine the rate of delivery of the drug from the polymer. Illustratively, the rate of delivery can be determined by measuring the transfer of drug from one chamber to another through cadaver skin over time, and calculating, from the obtained data, the drug delivery or flux rate.

In a particularly preferred embodiment of the invention, the multiple polymer adhesive system comprises a blend of an acrylic pressure-sensitive adhesive and a silicone pressure-sensitive adhesive. The acrylic-based polymer and silicone-based polymer are preferably in a ratio by weight, respectively, from about 2:98 to about 96:4, more preferably from about 2:98 to about 90:10, and even more preferably about 2:98 to about 86:14. The amount of acrylic-based polymer (hereinafter referred to broadly as a polyacrylate) and silicone-based polymer (hereinafter referred to broadly as a polysiloxane) is selected to modify the saturation concentration of the drug in the multiple polymer adhesive system in order to affect the rate of delivery of the drug from the system and through the skin.

The adjustment to the saturation concentration of the drug in the multiple polymer adhesive system can either be an increase or a decrease. It has been found that when a polyacrylate having an SP of about 21 $(J/cm^3)^{1/2}$ is used as the principal polymer of a nitroglycerin (SP about 27 $(J/cm^3)^{1/2}$) monolithic system, a significant increase in the transdermal permeation rate of nitroglycerin can be achieved by the addition of a polymer having a lower solubility parameter, for example a polysiloxane (SP about 15 $(J/cm^3)^{1/2}$). By reducing the "net" solubility parameter of the multiple polymer transdermal adhesive system, the difference between the solubility parameter of nitroglycerin and the multiple polymer adhesive system is increased. This increased solubility parameter difference results in a lower saturation concentration for nitroglycerin, and thereby a greater thermodynamic driving force. Conversely, the composition of the multiple polymer adhesive system can be selected so that the saturation concentration of the drug in the system is increased, so the rate of delivery is retarded, such as would be desirable for administration of scopolamine.

Advantageously, the method and composition of the present invention permit selectable loading of the drug in the transdermal drug delivery system. The concentration by weight of the drug in the dermal composition is preferably about 0.3 to about 50 percent, more preferably about 0.5 to about 40 percent, and even more preferably about 1.0 to about 30 percent. Irrespective of whether there is high-loading or low-loading of the drug into the dermal composition, the multiple polymer adhesive system of the present invention can be formulated to maintain acceptable shear, tack, and peel adhesive properties.

Although not wishing to be bound by theory, particularly in this case where the structure of the composition has not been analyzed, it is postulated that the polymers of varying solubility parameters, for example, the polysiloxane and the polyacrylate, result in a heterogenous mix, with the components of the polymeric mixture performing as a mutually interpenetrating polymeric network in the composition. In other words, the multiple polymer adhesive system is a mixture of essentially mutually insoluble or immiscible polymers in contradistinction to the typical prior art transdermal drug delivery systems derived from a single polymer or a solution of mutually soluble polymers.

In the practice of the preferred embodiment of the invention, the acrylic-based polymer can be any of the homopolymers, copolymers, terpolymers, and the like of various acrylic acids. In such preferred embodiments, the acrylic-based polymer constitutes preferably from about 2% to about 95% of the total weight of the total dermal composition, and preferably about 2% to about 90%, and more preferably about 2% to about 85%, the amount of acrylate polymer being dependent on the amount and type of drug used.

The acrylate polymers of this invention are polymers of one or more monomers of acrylic acids and other copolymerizable monomers. The acrylate polymers also include copolymers of alkyl acrylates and/or methacrylates and/or copolymerizable secondary monomers or monomers with functional groups. By varying the amount of each type of monomer added, the cohesive properties of the resulting acrylate polymer can be changed as is known in the art. In general, the acrylate polymer is composed of at least 50% by weight of an acrylate or alkyl acrylate monomer, from 0 to 20% of a functional monomer copolymerizable with the acrylate, and from 0 to 40% of other monomers.

Acrylate monomers which can be used include acrylic acid, methacrylic acid, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate.

Functional monomers, copolymerizable with the above alkyl acrylates or methacrylates, which can be used include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate.

Further details and examples of acrylic adhesives which are suitable in the practice of the invention are described in Satas, "Acrylic Adhesives," *Handbook of Pressure-Sensitive Adhesive Technology*, 2nd ed., pp. 396–456 (D. Satas, ed.), Van Nostrand Reinhold, New York (1989).

Suitable acrylic adhesives are commercially available and include the polyacrylate adhesives sold under the trademarks Duro-Tak 80-1194, Duro-Tak 80-1196, and Duro-Tak 80-1197 by National Starch and Chemical Corporation, Bridgewater, N.J.

Suitable polysiloxanes include silicone pressure-sensitive adhesives which are based on two major components: a polymer, or gum, and a tackifying resin. The polysiloxane adhesive is usually prepared by cross-linking the gum, typically a high molecular weight polydiorganosiloxane, with the resin, a three-dimensional silicate structure, via a condensation reaction in an appropriate organic solvent. The ratio of resin to polymer is the most important factor which can be adjusted in order to modify the physical properties of polysiloxane adhesives. Sobieski, et aL, "Silicone Pressure Sensitive Adhesives," *Handbook of Pressure-Sensitive Adhesive Technology*, 2nd ed., pp. 508–517 (D. Satas, ed.), Van Nostrand Reinhold, New York (1989).

Further details and examples of silicone pressure sensitive adhesives which are useful in the practice of this invention are described in the following U.S. Pat. Nos.: 4,591,622; 4,584,355; 4,585,836; and 4,655,767.

Suitable silicone pressure-sensitive adhesives are commercially available and include the silicone adhesives sold under the trademarks BIO-PSA X7-3027, BIO-PSA X7-4919, BIO-PSA X7-2685, and BIO-PSA X7-3122 by Dow Corning Corporation, Medical Products, Midland, Mich. BIO-PSA-3027 is particularly suitable for use in formulations containing amine-functional drugs, such as albuterol.

In the practice of a preferred embodiment of the invention, the polysiloxane constitutes preferably from about 4% to about 97% of the total weight of the total dermal composition, and preferably about 8% to about 97%, and more preferably about 14% to about 97%.

In practicing the invention, any bioactive agent may be included in the dermal composition. Illustratively the bioactive agent is a drug. Any drug which is capable of producing a pharmacological response, localized or systemic, irrespective of whether therapeutic, diagnostic, or prophylactic in nature, in plants or animals is within the contemplation of the invention. In addition to drugs, bioactive agents such as pesticides, insect repellents, sun screens, cosmetic agents, etc. are within the contemplation of the invention. It should be noted that the bioactive agents may be used singly or as a mixture of two or more such agents, and in amounts sufficient to prevent, cure, diagnose or treat a disease, as the case may be.

Exemplary active drugs that can be administered by the novel transdermal drug delivery system of this invention include, but are not limited to:

1. Cardioactive medications, illustratively, organic nitrates such as nitroglycerin, isosorbide dinitrate and, isosorbide mononitrates; quinidine sulfate; procainamide; thiazides such as bendroflumethiazide, chlorothiazide, and hydrochlorothyazide; nifedipine; nicardipine; adrenergic blocking agents, such as timolol, and propranolol; verapamil; diltiazem; captopril; clonidine and prazosin.

2. Androgenic steroids, such as, testosterone, methyltestosterone and fluoxymesterone.

3. Estrogens, such as conjugated estrogens, esterified estrogens, estropipate, 17β-estradiol, 17β-estradiol valerate, equilin, mestranol, estrone, estriol, 17β-ethinyl estradiol, and diethylstilbestrol.

4. Progestational agents, such as progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17-alpha-hydroxyprogesterone, dydrogesterone, dimethisterone, ethinylestrenol, norgestrel, demegestone, promegestone, and megestrol acetate.

5. Drugs having an action on the central nervous system, for example sedatives, hyponotics, antianxiety agents, analgesics and anesthetics, such as chloral, buprenorphine, naloxone, haloperidol, fluphenazine, pentobarbital, phenobarbital, secobarbital, codeine, lidocaine, tetracaine, dyclonine, dibucaine, cocaine, procaine, mepivacaine, bupivacaine, etidocaine, prilocaine, benzocaine, fentanyl, and nicotine.

6. Nutritional agents, such as vitamins, essential amino acids and essential fats.

7. Anti-inflammatory agents, such as hydrocortisone, cortisone, dexamethasone, fluocinolone, triamcinolone, medrysone, prednisolone, flurandrenolide, prednisone, halcinonide, methylprednisolone, flurandrenolide, prednisone, halcinonide, methylprednisolone, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, tolmetin, and the like.

8. Antihistamines, such as diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine, and chlorpheniramine.

9. Respiratory agents, such as theophilline and $\beta_2$-adrenergic agonists such as albuterol, terbutaline, metaproterenol, ritodrine, carbuterol, fenoterol, quinterenol, rimiterol, solmefamol, soterenol, and tretoquinol.

10. Sympathomimetics such as dopamine, norepinephrine, phenylpropanolamine, phenylephrine, pseudoephedrine, amphetamine, propylhexedrine and epinephrine.

11. Miotics, such as pilocarpine, and the like;

12. Cholinergic agonists, such as choline, acetylcholine, methacholine, carbachol, bethanechol, pilocarpine, muscarine, and arecoline.

13. Antimuscarinic or muscarinic cholinergic blocking agents, such as atropine, scopolamine, homatropine, methscopolarnine, homatropine methylbromide, methantheline, cyclopentolate, tropicamide, propantheline, anisotropine, dicyclomine, and eucatropine.

14. Mydriatics, such as atropine, cyclopentolate, homatropine, scopolamine, tropicamide, eucatropine and hydroxyamphetamine.

15. Psychic energizers, such as 3-(2-aminopropy)indole, 3-(2-aminobutyl)indole, and the like.

16. Anti-infectives, such as antibiotics, including penicillin, tetracycline, chloramphenicol, sulfacetamide, sulfamethazine, sulfadiazine, sulfamerazine, sulfamethizole and sulfisoxazole; antivirals, including idoxuridine; antibacterials, such as erythromycin and clarithromycin; and other anti-infectives including nitrofurazone and the like.

17. Dermatological agents, such as vitamins A and E.

18. Humoral agents, such as the prostaglandins, natural and synthetic, for example PGE1, PGE 2-alpha, and PGF 2-alpha, and the PGE1 analog misoprostol.

19. Antispasmodics, such as atropine, methantheline, papaverine, cinnamedrine, and methscopolamine.

20. Antidepressant drugs, such as isocarboxazid, phenelzine, tranylcyprornine, imipramine, amitriptyline, trimipramine, doxepin, desipramine, nortriptyline, protriptyline, amoxapine, maprotiline, and trazodone.

21. Anti-diabetics, such as insulin, and anticancer drugs such as tamoxifen and methotrexate.

22. Anorectic drugs, such as, dextroamphetamine, methamphetamine, phenylpropanolamine, fenfluramine, diethylpropion, mazindol, and phentermine.

23. Anti-allergenics, such as antazoline, methapyrilene, chlorpheniramine, pyrilamine and pheniramine.

24. Tranquilizers, such as reserpine, chlorpromazine, and antianxiety benzo-diazepines such as alprazolam, chlordiazepoxide, clorazeptate, halazepam, oxazepam, prazepam, clonazepam, flurazepam, triazolam, lorazepam and diazepam.

25. Antipsychotics, such as thiopropazate, chlorpromazine, triflupromazine, mesoridazine, piperacetazine, thioridazine, acetophenazine, fluphenazine, perphenazine, trifluoperazine, chlorprothixene, thiothixene, haloperidol, bromperidol, loxapine, and molindone.

26. Decongestants, such as phenylephrine, ephedrine, naphazoline, tetrahydrozoline.

27. Antipyretics, such as aspirin, salicylamide, and the like.

28. Antimigrane agents, such as dihydroergotarnine and pizotyline.

29. Drugs for treating nausea and vomiting, such as chlorpromazine, perphenazine, prochlorperazine, promethazine, triethylperazine, triflupromazine, and trirneprazine.

30. Anti-malarials, such as the 4-aminoquinolines, alphaaminoquinolines, chloroquine, and pyrimethamine.

31. Anti-ulcerative agents, such as misoprostol, omeprazole, and enprostil.

32. Peptides, such as growth releasing factor.

33. Drugs for Parkinson's disease, spasticity, and acute muscle spasms such as levodopa, carbidopa, amantadine, apomorphine, bromocriptine, selegiline (deprenyl), trihexyphenidyl hydrochloride, benztropine mesylate, procyclidine hydrochloride, baclofen, diazepam, and dantrolene.

34. Anti-estrogen or hormone agents, such as tamoxifen or human chorionic gonadotropin.

The active agents can be present in the composition in different forms, depending on which form yields the optimum delivery characteristics. Thus, in the case of drugs, the drug can be in its free base or acid form, or in the form of salts, esters, or any other pharmacologically acceptable derivatives, or as components of molecular complexes.

The amount of drug to be incorporated in the composition varies depending on the particular drug, the desired therapeutic effect, and the time span for which the device is to provide therapy. For most drugs, the passage of the drugs through the skin will be the rate-limiting step in delivery. Thus, the amount of drug and the rate of release is typically selected so as to provide transdermal delivery characterized by a zero order time dependency for a prolonged period of time. The minimum amount of drug in the system is selected based on the amount of drug which passes through the skin in the time span for which the device is to provide therapy. Normally, the amount of drug in the system can vary from about 0.3% to about 50% by weight, and preferably, for the lower drug doses permitted by this invention, from about 1.0% to about 30%.

Of course, the composition of the transdermal drug delivery system can also contain agents known to accelerate the delivery of the drug through the skin. These agents have been referred to as skin-penetration enhancers, accelerants, adjuvants, and sorption promoters, and are collectively referred herein as "enhancers." This class of agents includes those with diverse mechanisms of action including those which have the function of improving the solubility and diffusibility of the drug within the multiple polymer and those which improve percutaneous absorption, for example, by changing the ability of the stratum corneum to retain moisture, softening the skin, improving the skin's permeability, acting as penetration assistants or hair-follicle openers or changing the state of the skin including the boundary layer. Some of these agents have more than one mechanism of action, but in essence they serve to enhance the delivery of the drug.

Some examples of enhancers are polyhydric alcohols such as dipropylene glycol, propylene glycol, and polyethylene glycol which enhance drug solubility; oils such as olive oil, squalene, and lanolin; fatty ethers such as cetyl ether and oleyl ether; fatty acid esters such as isopropyl myristate which enhance drug diffusibility; urea and urea derivatives such as allantoin which affect the ability of keratin to retain moisture; polar solvents such as dimethyldecylphosphoxide, methyloctyl-sulfoxide, dimethyllaurylamide, dodecylpyrrolidone, isosorbitol, dimethyl-acetonide, dimethylsulfoxide, decylmethyl-sulfoxide, and dimethylformarnide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, and isopropyl palmitate.

In certain embodiments of the invention a plasticizer or tackifying agent is incorporated into the formulation to improve the adhesive characteristics of the dermal composition. A tackifying agent is particularly useful in those embodiments in which the drug does not plasticize the polymer. Suitable tackifying agents are those known in the art including: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; and (7) hydrogenated wood rosins. The tackifying agent employed is preferably compatible with the blend of polymers. In preferred embodiments, the tackifying agent is silicone fluid (e.g., 360 Medical Fluid, available from Dow Corning Corporation, Midland, Mich.) or mineral oil. Silicone fluid is useful for blends comprising polysiloxane as a major component. In other embodiments, where polyacrylate, for example, is a major component, mineral oil is a preferred tackifying agent.

Some drugs, such as the vasodilator nitroglycerin, function as plasticizers in the composition because they are soluble to a certain degree in the polymers comprising the system. For drug molecules which are not readily soluble in the polymer system, a co-solvent for the drug and polymer can be added. Co-solvents, such as lecithin, retinol derivatives, tocopherol, dipropylene glycol, triacetin, propylene glycol, saturated and unsaturated fatty acids, mineral oil, silicone fluid, alcohols, butyl benzyl phthalate, and the like are useful in the practice of the instant invention depending on the solubility of the drug in the multiple polymer adhesive system.

To summarize, the preferred and optimum compositions for the polyacrylate/polysiloxane embodiment are as follows:

TABLE II

| | PERCENT BY WEIGHT | |
|---|---|---|
| Component | Preferred Range | Optimum Range |
| Polysiloxane | 97–4 | 97–14 |
| Polyacrylate | 2–95 | 2–85 |
| Co-solvent(s) | 0–30 | 0–20 |
| Enhancer(s) | 0–20 | 0–10 |
| Drug(s) | 0.3–50 | 1–30 |

The composition of this invention may further be provided with various thickeners, fillers and other additives known for use with dermal compositions. Where the composition tends to absorb water, for example, when lecithin is used as a co-solvent, hydrophilic fillers are especially useful. One type of hydrophilic filler which has been successfully employed is an aluminum silicate clay.

In a device aspect of the invention, the dermal composition can be used as an adhesive portion of any transdermal drug delivery device (e.g. a reservoir device) or it can comprise an adhesive monolithic device. Of course, the principles of the invention would still apply to embodiments where the dermal composition is not a pressure-sensitive adhesive and comprises the drug reservoir.

Figure 1:
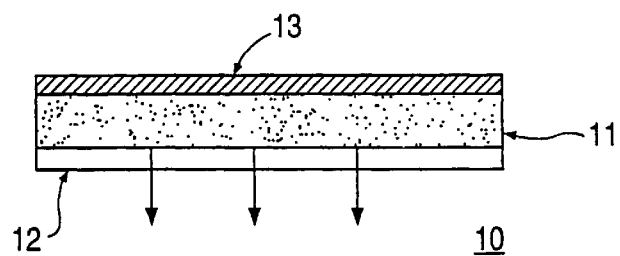
FIG. 1 is a schematic illustration of a monolithic transdermal drug delivery device of the present invention.

Reference to FIG. 1 shows a schematic illustration of an adhesive monolithic device embodiment of the invention 10. The dermal composition comprises a monolithic body 11 of a defined geometric shape with a protective release liner 12 on one side of monolithic body 11 and a backing layer 13 on the other side. Removal of the release liner 12 exposes the pressure-sensitive multiple polymer adhesive which functions both as the drug carrier matrix and as the means of applying the system to the patient.

A device, or individual dosage unit, of the present invention can be produced in any manner known to those of skill in the art. After the dermal composition is formed, it may be brought into contact with the backing layer in any manner known to those of skill in the art. Such techniques include calender coating, hot melt coating, solution coating, etc. Of course, backing materials are well known in the art and can comprise plastic films of polyethylene, vinyl acetate resins, ethylene/vinyl acetate copolymers, polyvinyl chloride, polyurethane, and the like, metal foils, non-woven fabric, cloth and commercially available laminates. The backing material generally has a thickness in the range of 2 to 1000 micrometers and the dermal composition is generally disposed on backing material in a thickness ranging from about 12 to 250 micrometers thick.

Suitable release liners are also well known in the art and include the commercially available products of Dow Corning Corporation designated Bio-Release® liner and Syloff® 7610 liner. For preferred embodiments in which a polysiloxane is part of the multiple polymeric adhesive system, the release liner must be compatible with the silicone adhesive. An example of a suitable commercially available liner is 3M's 1022 Scotch Pak.

The configuration of the transdermal delivery system of the present invention can be in any shape or size as is necessary or desirable. Illustratively, a single dosage unit may have a surface area in the range of 1 to 200 cm². Preferred sizes are: from 5 to 60 cm².

In a method aspect of the invention, a plurality of polymers having differing solubility parameters are blended (but not chemically reacted or cross-linked) to result in a dermal composition, or multiple polymer adhesive system with incorporated drug or bioactive agent, which controls delivery of an incorporated drug into and through the epidermis. The blending of polymers results in an adjustment of the saturation concentration of the drug in the polymeric system and therefore permits selective modulation of the transdermal drug delivery rate. The term "blending," of course, incorporates choosing the appropriate polymeric components, and the proportions thereof, to achieve the desired effect.

In a preferred embodiment of the invention, a dermal composition is prepared, for example, by mixing the polyacrylate, the polysiloxane, drug, co-solvent(s), and tackifying agent, if needed, in an appropriate volatile solvent (s), then casting the mixture and removing the solvent(s) by evaporation to form a film.

Suitable volatile solvents include, but are not limited to, alcohols such as isopropanol and ethanol; aromatics such as xylenes and toluene; aliphatics such as hexane, cyclohexane, and heptane; and alkanoic acid esters such as ethyl acetate and butyl acetate.

An exemplary general method of preparation is as follows:

1. Appropriate amounts of polysiloxane and polyacrylate, dissolved in a solvent(s), are combined and thoroughly mixed together in a vessel.

2. The drug is then added to the polymer mixture and agitation is carried out until the drug is uniformly mixed in.

3. Co-solvents and enhancers, if necessary, can then be added to the drug-polymer mixture, and thoroughly mixed.

4. The formulation is then transferred to a coating operation where it is coated onto a protective release liner at a controlled specified thickness.

5. The coated product is then passed through an oven in order to drive off all volatile processing solvents.

6. The dried product on the release liner is then joined to the backing material and wound into rolls for storage.

7. Appropriate size and shape dosage units are die-cut from the roll material and then pouched.

The order of steps, the amounts of ingredients, and the amount and time of agitation or mixing are process variables which will depend on the specific polymers, drug, co-solvents, and enhancers used in the formulation. These factors can be adjusted by those of skill in the art as required to provide a uniform product which has acceptable pressure-sensitive adhesive characteristics.

EXAMPLES

The following specific examples are included as illustrative of dermal compositions, and methods of making same, within the contemplation of the invention. These examples are in no way intended to be limiting of the scope of the invention.

The following commercially available adhesives were used in the blends comprising the multiple polymer adhesive system of the examples: "Duro-Tak 80-1194, 80-1196, and 80-1197" are trademarks of National Starch and Chernical Corporation, Bridgewater, N.J. for acrylic adhesives (polyacrylates) in organic solutions.

"BIO-PSA X7-3027, X7-4919, X7-2685, and X7-3122" are trademarks of Dow Corning Corporation, Medical Products, Midland, Mich. for silicone adhesives (polysiloxanes) in organic solutions. BIO-PSA-3027 is particularly suitable for use in formulations containing amine-functional drugs, such as albuterol and pilocarpine, in the following examples.

"Vistanex LM-LS-LC" is a trademark of Exxon Chemical Company, Houston, Tex., for a polyisobutylene polymer with a Flory molecular weight of 42,600 to 46,100.

"Elvax 40-W" is a trademark of Du Pont Company, Wilmington, Del., for a polyethylene/vinyl acetate copolymer (40% vinyl acetate content).

The aforementioned polymeric adhesives are supplied, or prepared, as solutions wherein the percent solids by weight are as follows:

| Ingredient | Percent Solids |
| --- | --- |
| BIO-PSA X7-3027 | 50 |
| BIO-PSA X7-3122 | 65 |
| BIO-PSA X7-4919 | 50 |
| BIO-PSA X7-2685 | 50 |
| Duro-Tak 80-1194 | 45 |
| Duro-Tak 80-1196 | 45 |
| Duro-Tak 80-1197 | 45 |
| Elvax 40-W | 30 |
| Vistanex LM-MS-LC | 30 |

"360 Medical Fluid" is a trademark of Dow Corning Corporation for a polydimethylsiloxane fluid. In certain embodiments of the invention, 360 Medical Fluid is added as a tackifier to improve the adhesive characteristics of the end product.

Example 1

A nitroglycerin-polymer mixture was prepared by combining 22.0 parts of nitroglycerin, 1.0 part of dipropylene glycol, 1.3 parts of lecithin, 0.8 parts of propylene glycol, 2.5 parts of 360 Medial Fluid (1000 cs), 1.0 part of bentonite, 63.6 parts of polyacrylate (Duro-Tak 80-1194), and 85.6 parts of polysiloxane (BIO-PSA X7-4919), and mixed well in an appropriate container. Nitroglycerin is available as a solution in solvents such as, ethanol, toluene, and propylene glycol from ICI Americas Inc., Wilmington, Del. In this instance, the nitroglycerin was added as a solution in toluene mixed together with the polyacrylate. The resulting composition had the ingredient concentrations on a "dry" basis, that is, after removal of volatile process solvents, shown below.

| COMPONENT | PERCENT BY WEIGHT |
| --- | --- |
| Polysiloxane | 42.8 |
| (Dow Corning Silicone Adhesive X7-4919) | |
| Polyacrylate | 28.6 |
| (National Starch Acrylic Adhesive, Duro-Tak 80-1194) | |
| Polydimethylsiloxane fluid | 2.5 |
| (Dow Corning 360 Medical Fluid) | |
| Lecithin | 1.3 |
| Propylene glycol | 0.8 |
| Dipropylene glycol | 1.0 |
| Bentonite | 1.0 |
| Nitroglycerin | 22.0 |
| | 100.0 |

Figure 2:
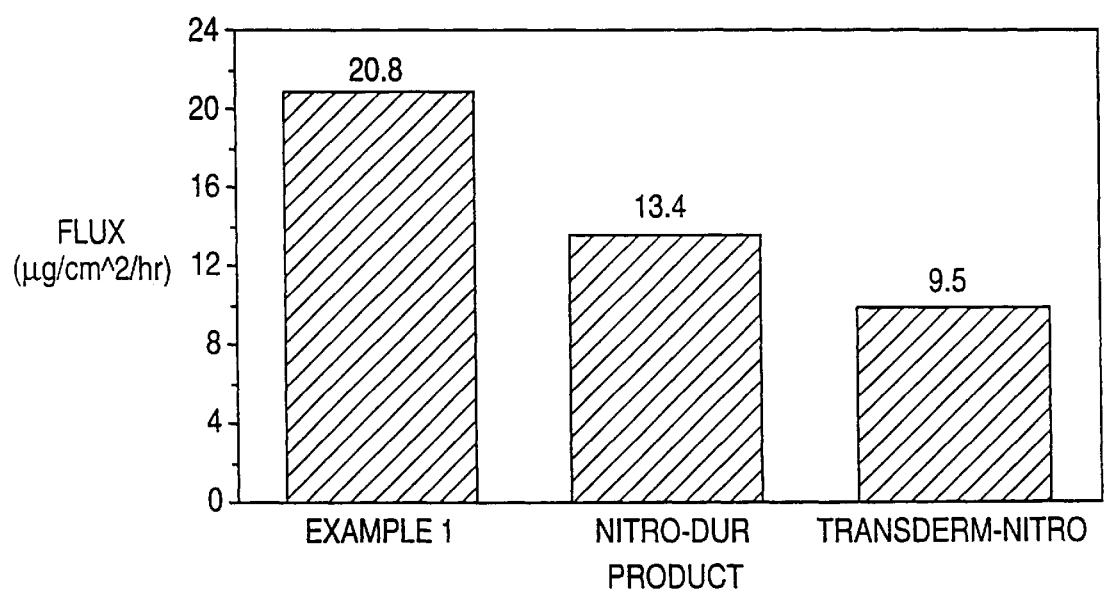
FIG. 2 is a graphic representation of the steady-state nitroglycerin flux rates through cadaver skin in vitro from a transdermal drug delivery composition of the present invention (formulation of Example 1) and two commercially-available ritroglycerin-containing transdermal delivery devices: Transderm-Nitro® (a trademark of Ciba-Geigy Corporation, Summit, N.J.), and Nitro-Dur® (a trademark of Key Pharmaceuticals, Inc., Kenilworth, N.J.)

Nitroglycerin flux results through cadaver skin in vitro from the formulation of Example 1, Transderm-Nitro® (a trademark of Ciba-Geigy Corporation, Summit, N.J.), and Nitro-Dur® (a trademark of Key Pharmaceuticals, Inc., Kenilworth, N.J.) are summarized in FIG. 2. As shown in FIG. 2, nitroglycerin flux from the dermal composition of Example 1 (20.8 $\mu g/cm^2 hr$) was approximately twice that from Transderm-Nitro® (9.5 $\mu g/cm^2 hr$) and about 1.5 times that from Nitro-Dur® (13.4 $\mu g/cm^2 hr$).

Examples 2–5

In the following examples (2–5), the method of Example 1 was used with the appropriate amounts of starting materials to yield compositions having the following ingredient concentrations set forth in tabular form in TABLE III. Example 2 is presented for comparative purposes and its formulation is not within the scope of the present invention. Example 3 and 5 are adhesive compositions comprising blends of polyacrylate and a second polymer selected to illustrate the principles of the invention. All other components, such as excipients or fillers, remain constant in composition and amount from Examples 2 to 5.

TABLE III

| Ingredient (SP, $J^{1/2}/cm^{3/2}$) | Examples (%, w/w) | | | |
|---|---|---|---|---|
| | 2 | 3 | 4 | 5 |
| Polyacrylate (21) | 73.2 | 33.1 | 33.1 | 33.1 |
| Polyethylene vinyl acetate (21) | — | 40.1 | — | — |
| Polyisobutylene (17) | — | — | 40.1 | — |
| Polysiloxane (15) | — | — | — | 40.1 |
| Nitroglycerin (27) | 20.8 | 20.8 | 20.8 | 20.8 |
| Oleic acid | 2.0 | 2.0 | 2.0 | 2.0 |
| Propylene glycol | 0.8 | 0.8 | 0.8 | 0.8 |
| Lecithin | 1.2 | 1.2 | 1.2 | 1.2 |
| Dipropylene glycol | 1.0 | 1.0 | 1.0 | 1.0 |
| Bentonite | 1.0 | 1.0 | 1.0 | 1.0 |

Figure 3:
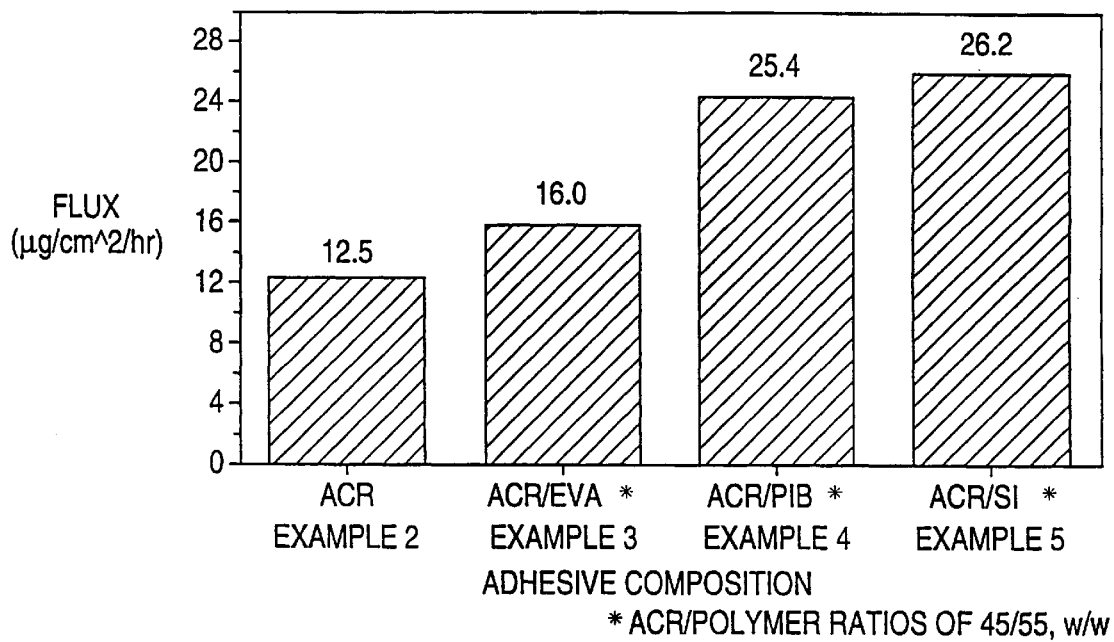
FIG. 3 is a graphical representation which summarizes in vitro nitroglycerin flux results through cadaver skin for the polymeric systems of Examples 2–5. The composition of Example 2 (polyacrylate-only adhesive) is compared to the multiple polymer compositions of Examples 3, 4, and 5, in which the polyacrylate is blended with a polyethylene vinyl acetate, a polyisobutylene, and a polysiloxane, respectively.

FIG. 3 graphically summarizes the in vitro nitroglycerin flux results through cadaver epidermis from the dermal compositions of Examples 2 to 5. As seen in FIG. 3, addition of either polyisobutylene (Example 4) or polysiloxane (Example 5)—both with SPs lower than polyacrylate—resulted in doubling of the nitroglycerin flux as compared to an all acrylate system (Example 2). However, addition of polyethylene vinyl acetate (Example 3)—with an SP value similar to the polyacrylate—resulted in little effect on nitroglycerin flux as compared to the system of Example 2. Thus, the formulation of Example 3 is not within the scope of the present invention.

Example 6

A series of nitroglycerin-containing compositions (I–VI) were prepared in which the polyacrylate (X7-3122) to polysiloxane (Duro-Tak 80-1194) ratio was varied from 100.0:0.0 (all acrylic) to 0.0:100.0 (all siloxane) by weight. Nitroglycerin concentration was held at 20% for all compositions. The ingredient concentrations of these compositions are shown below in TABLE IV.

TABLE IV

| | I | II | III | IV | V | VI |
|---|---|---|---|---|---|---|
| Polysiloxane | — | 14.4 | 28.8 | 43.2 | 57.6 | 72.6 |
| Silicone Fluid | — | 1.6 | 3.2 | 4.8 | 6.4 | 8.0 |
| Polyacrylate | 80.0 | 64.0 | 48.0 | 32.8 | 16.0 | — |
| Nitroglycerin | 20.0 | 20.0 | 20.0 | 20.0 | 20.0 | 20.0 |

Figure 4:
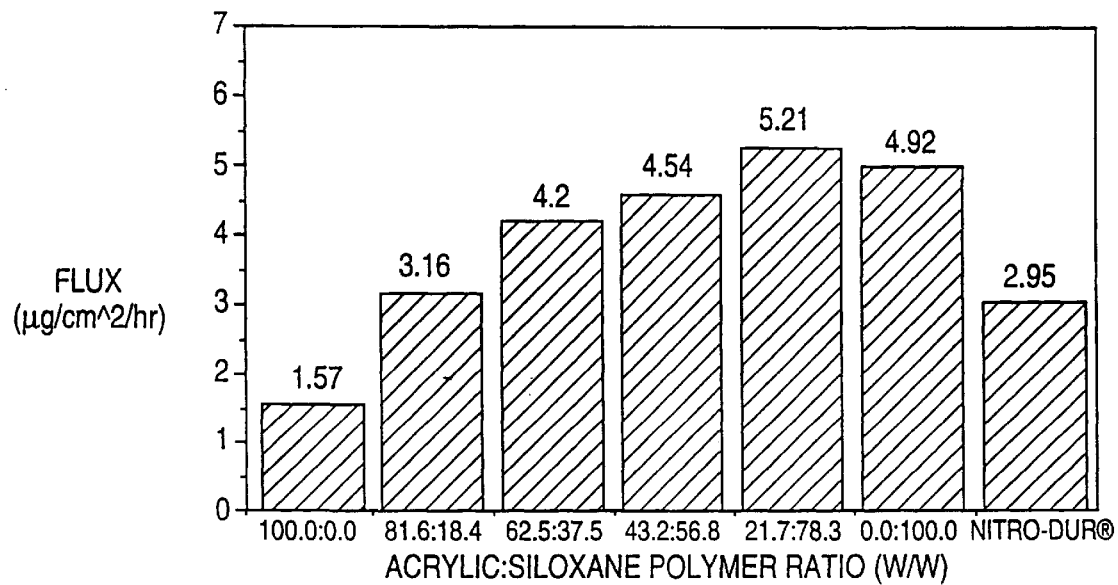
FIG. 4 is a graphical representation of the steady-state nitroglycerin flux through cadaver skin in vitro from a multiple polymer transdermal adhesive system of Example 6 comprising various weight ratios of polyacrylate and polysiloxane.

In vitro skin flux was determined for these compositions and the results are summarized in Table V and graphically depicted in FIG. 4.

TABLE V

| | % of Polymer | | (µg/cm 2/hr) | (hr) |
|---|---|---|---|---|
| Composition | Polyacrylate | Polysiloxane | GTN Flux | Tlag |
| I | 100 | 0 | 1.6 | 0.0 |
| II | 81.6 | 18.4 | 3.2 | 1.5 |

TABLE V-continued

| | % of Polymer | | (µg/cm 2/hr) | (hr) |
|---|---|---|---|---|
| Composition | Polyacrylate | Polysiloxane | GTN Flux | Tlag |
| III | 62.5 | 37.5 | 4.2 | 2.0 |
| IV | 43.2 | 56.8 | 4.5 | 2.3 |
| V | 21.7 | 78.3 | 5.2 | 2.3 |
| VI | 0 | 100 | 4.9 | 2.4 |
| Nitro-Dur ® | — | — | 3.0 | 2.5 |

As shown, nitroglycerin (GTN) flux increased as the concentration of polysiloxane in the multiple polymer adhesive matrix increased up to a maximum, at around 80% polysiloxane, after which no more increase in flux was seen. It appears that beyond a certain concentration of siloxane polymer, the nitroglycerin activity ceases to increase (unit activity is reached), and the flux no longer increases. The attainment of saturation concentration (unit activity) is further verified by the fact that Composition VI had nitroglycerin exudate; that is, the surface of the adhesive was "wet" with excess nitroglycerin. Of course, Composition VI, which is all polysiloxane, is not within the contemplation of the invention.

The composition of the blend of polymers is preferably chosen so that the flux rate of drug from the blend is at a maximum. Studies similar to those reported herein may be employed to assist in selecting the appropriate components of the blend and the weight ratios thereof. In alternative embodiments, it may be desirable to select a composition in which the flux rate will be retarded.

Examples 7–9

An estradiol-polymer mixture (Example 7) was prepared by combining 2.0 parts of 17-β-estradiol, 2.0 parts of propylene glycol, 3.0 parts of lecithin, 5.0 parts of oleic acid, 5.0 parts of dipropylene glycol, 93.3 parts of polyacrylate (Duro-Tak 80-1196), and 63.1 parts of polysiloxane (BIO-PSA X7-3122), and mixing well in an appropriate container. The resulting composition had the ingredient concentrations on a "dry" basis, that is, after removal of volatile process solvents, given below in TABLE VI.

Examples 8 and 9 were made in accordance with the method of Example 7. The compositions of Examples 8 and 9 have the same drug and additional components, such as the co-solvents, as Example 7, but are not within the scope of this invention inasmuch as the resulting adhesive matrices are single polymer systems. Examples 8 and 9 are given for comparative purposes only.

TABLE VI

| | Examples (%, w/w) | | |
|---|---|---|---|
| Ingredient | 7 | 8 | 9 |
| Polyacrylate | 42.0 | 83.0 | — |
| Polysiloxane | 41.0 | — | 83.0 |
| Estradiol | 2.0 | 2.0 | 2.0 |
| Oleic acid | 5.0 | 5.0 | 5.0 |
| Propylene glycol | 2.0 | 2.0 | 2.0 |
| Lecithin | 3.0 | 3.0 | 3.0 |
| Dipropylene glycol | 5.0 | 5.0 | 5.0 |

Figure 5:
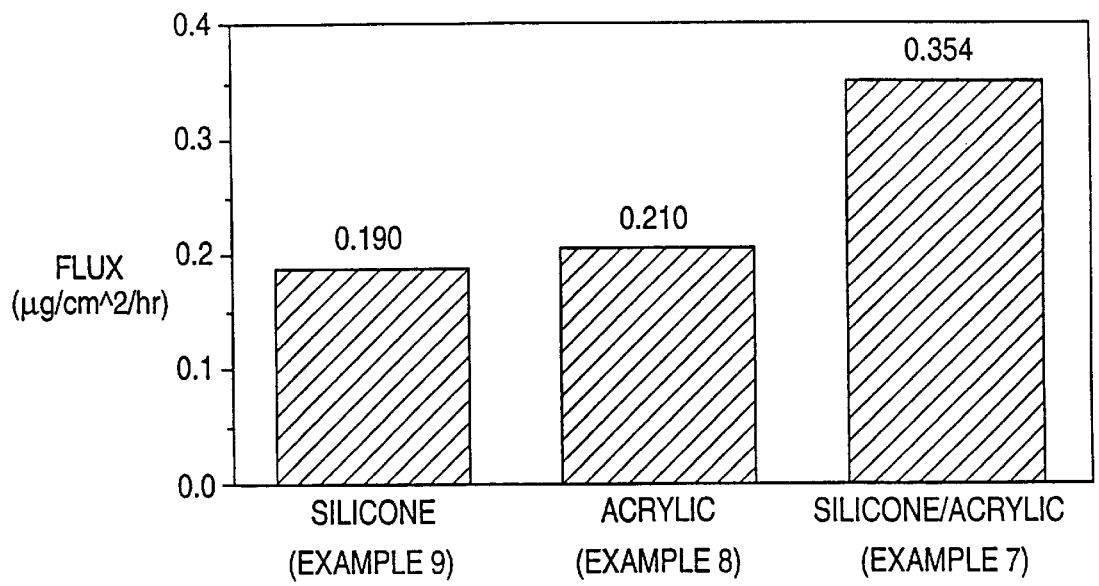
FIG. 5 is a graphical representation of steady-state estradiol flux through cadaver skin in vitro from the drug delivery systems of the prior art, specifically single polymeric adhesives of silicone and acrylic, as compared to a multiple polymer transdermal adhesive system (polyacrylate/polysiloxane) of the present invention.

Estradiol flux in vitro from the systems of Examples 7, 8, and 9 is shown in FIG. 5. As seen in FIG. 5, delivery from the system of this invention utilizing the multiple polymer adhesive (polyacrylate/polysiloxane) of Example 7 was substantially greater than delivery from the prior art systems comprising single polymer adhesives (Examples 8 and 9).

Examples 10–13

In the following examples (10–13), the method of Example 7 was used with the appropriate amounts of starting materials to yield compositions having the ingredient concentrations set forth in TABLE VII.

TABLE VII

| Ingredient | Examples (%, w/w) | | | |
|---|---|---|---|---|
| | 10 | 11 | 12 | 13 |
| Polysiloxane | 18.0 | 33.5 | 39.5 | 58.0 |
| Polyacrylate | 65.0 | 39.5 | 33.5 | 15.0 |
| Estradiol | 2.0 | 2.0 | 2.0 | 2.0 |
| Oleic acid | 5.0 | 5.0 | 5.0 | 5.0 |
| Propylene glycol | 2.0 | 2.0 | 2.0 | 2.0 |
| Lecithin | 3.0 | 3.0 | 3.0 | 3.0 |
| Silicone fluid | 5.0 | 15.0 | 15.0 | 15.0 |

Figure 6:
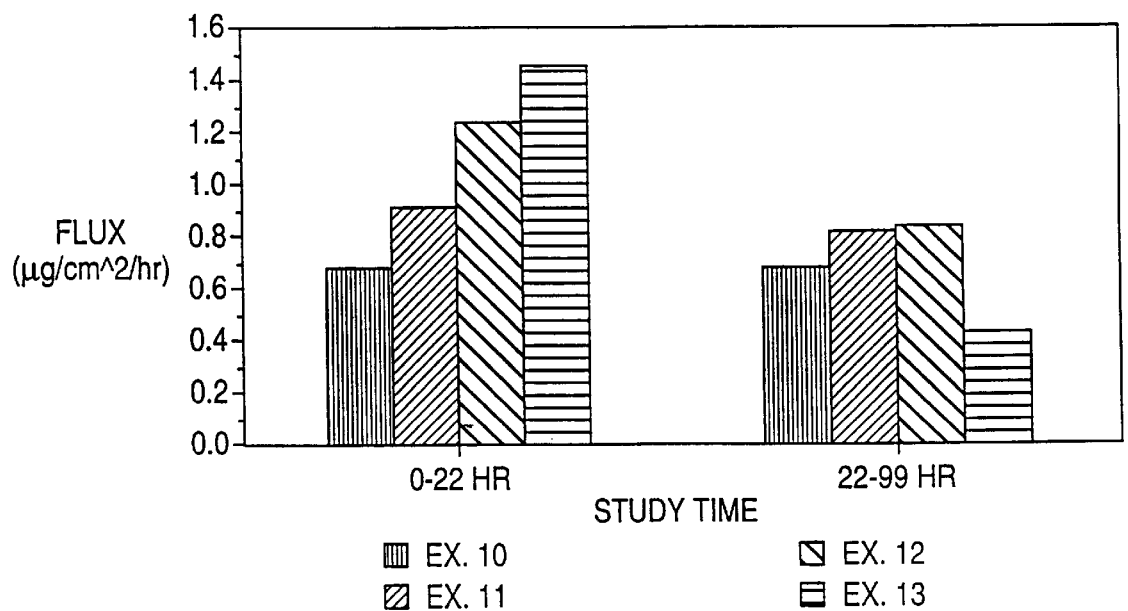
FIG. 6 is a graphical representation of average estradiol flux through cadaver skin in vitro from 0 to 22 hours and from 22 to 99 hours for a multiple polymer transdermal adhesive system comprising various weight ratios of polyacrylate and polysiloxane.

FIG. 6 shows estradiol flux results for the compositions of Examples 10–13; average flux was calculated for each composition from 0 to 22 hours and from 22 to 99 hours from the start of the study. As seen in FIG. 6, estradiol flux progressively increased with increased silicone polymer content during the first 22 hours of delivery, but was affected to a much lesser degree during the remainder of the study (22 to 99 hours). Thus, significant adjustment of the estradiol delivery rate during the initial phase of delivery was accomplished, with minor effects on the later delivery phase, by modulating the polysiloxane to polyacrylate polymer ratio. FIG. 6 also illustrates that the delivery characteristics over time can be adjusted by the appropriate choice of polymers and respective weight ratios. For example, the formulation of Example 10 delivers drug at approximately the same rate over time whereas the formulation of Example 13 delivers more quickly in the early phase than the latter.

Examples 14–16

A norethindrone acetate-polymer mixture was prepared by combining 0.6 parts of norethindrone acetate, 1.0 parts of butylene glycol, and 40.9 parts of polyacrylate (Duro-Tak 80-1194), and mixing well in an appropriate container. The resulting composition had the ingredient concentrations on a "dry" basis, that is, after removal of volatile process solvents, given below in TABLE VIII. The same method was employed to make Examples 15 and 16.

TABLE VIII

| Ingredient | Examples (% w/w) | | |
|---|---|---|---|
| | 14 | 15 | 16 |
| Polyacrylate | 92.0 | — | 46.0 |
| Polysiloxane | — | 92.0 | 46.0 |
| Norethindrone acetate | 3.0 | 3.0 | 3.0 |
| Butylene glycol | 5.0 | 5.0 | 5.0 |

Figure 7:
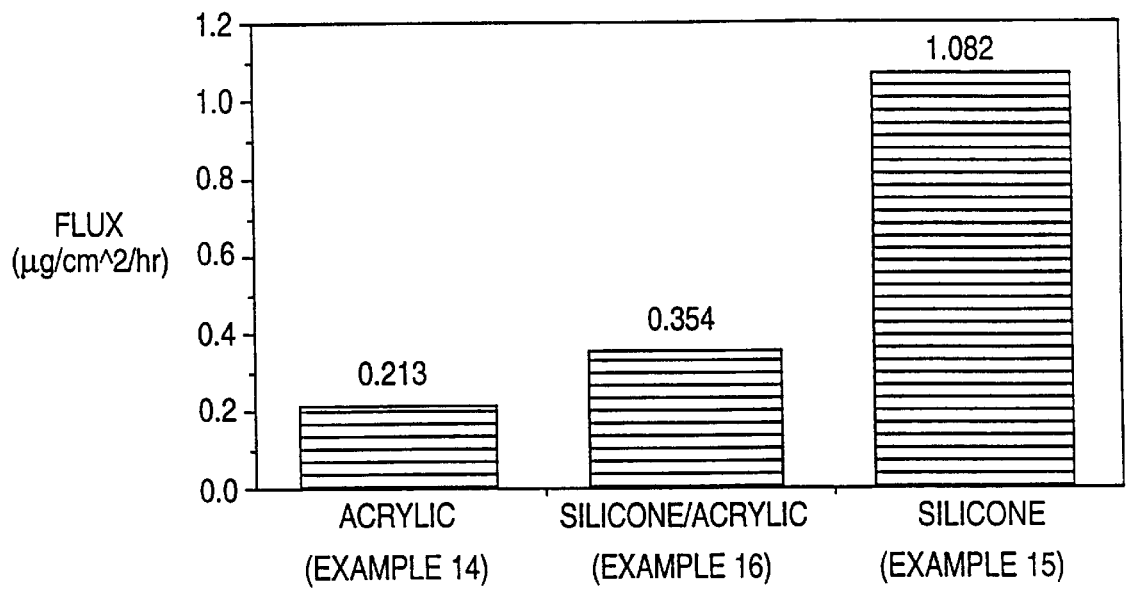
FIG. 7 is a graphical representation of steady-state norethindrone acetate flux through cadaver skin in vitro from the drug delivery systems of the prior art, specifically single polymeric adhesives of silicone and acrylic, as compared to a multiple polymer transdermal adhesive system (polyacrylate/polysiloxane) of the present invention.

Norethindrone acetate flux in vitro from the systems of Examples 14, 15, and 16 is shown in FIG. 7. As seen in FIG. 7, norethindrone acetate delivery from the polyacrylate/polysiloxane systems of this invention (Example 16) was intermediate to delivery from the single polymer systems not of this invention (Example 14 and 15). Thus, blending the polyacrylate and polysiloxane results in modulation of the norethindrone acetate flux.

Examples 17–20

As estradiol/norethindrone acetate combination-polymer mixture was prepared by combining 0.6 parts of 17β-estradiol, 0.6 parts of norethindrone acetate, 0.6 parts of butylene glycol, 0.6 parts of oleic acid, 1.5 parts of lecithin, 4.5 parts of silicone fluid (polydimethylsiloxane fluid, Dow Corning 360 Medical Fluid, 100 cs), and 43.2 parts of polysiloxane (BIO-PSA X7-4919), and mixing well in an appropriate container. The method of Example 17 was used with the appropriate amounts of starting materials to yield the compositions of Example 18, 19 and 20. The polyacrylate used in Examples 18-20 was National Starch Acrylic Adhesive, Duro-Tak 80-1197. The resulting compositions had the ingredient concentrations on a "dry" basis, that is, after removal of volatile process solvents, given below in TABLE IX.

TABLE IX

| Ingredient | Examples (% w/w) | | | |
|---|---|---|---|---|
| | 17 | 18 | 19 | 20 |
| Polysiloxane | 72.0 | 68.0 | 60.0 | 47.0 |
| Polyacrylate | — | 5.0 | 15.0 | 30.0 |
| Estradiol | 2.0 | 2.0 | 2.0 | 2.0 |
| Norethindrone acetate | 2.0 | 2.0 | 2.0 | 2.0 |
| Oleic acid | 2.0 | 2.0 | 2.0 | 2.0 |
| Butylene glycol | 2.0 | 2.0 | 2.0 | 2.0 |
| Lecithin | 5.0 | 5.0 | 5.0 | 5.0 |
| Silicone fluid | 15.0 | 14.0 | 12.0 | 10.0 |

Figure 8:
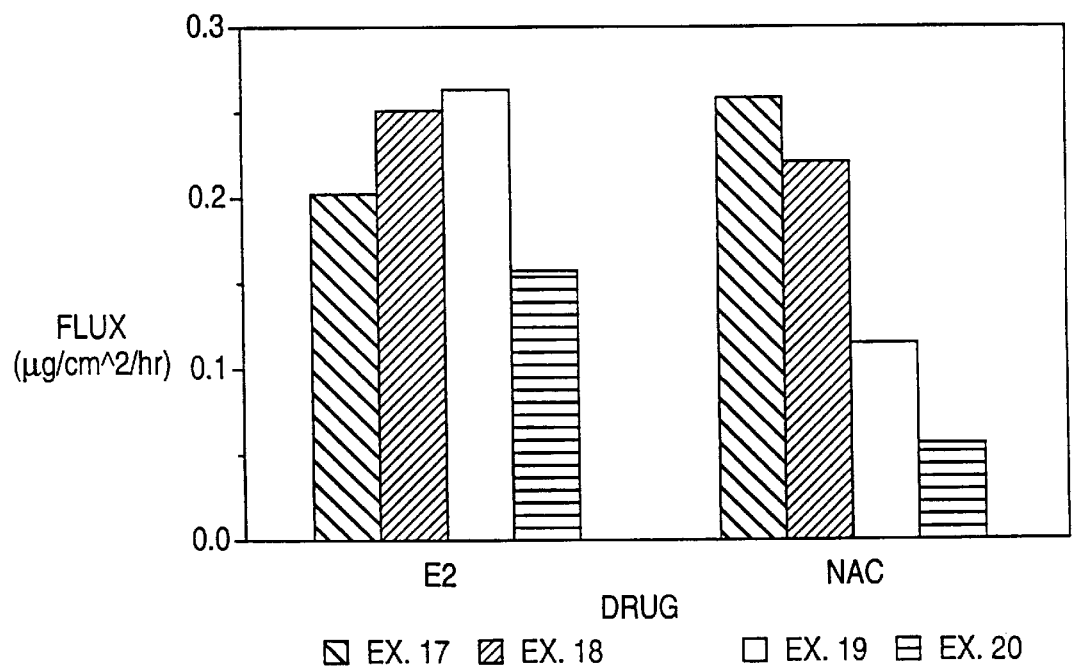
FIG. 8 is a graphical representation of average estradiol and norethindrone acetate flux through cadaver skin in vitro for a multiple polymer transdermal adhesive system comprising both drugs and various weight ratios of polyacrylate and polysiloxane.
Figure 9:
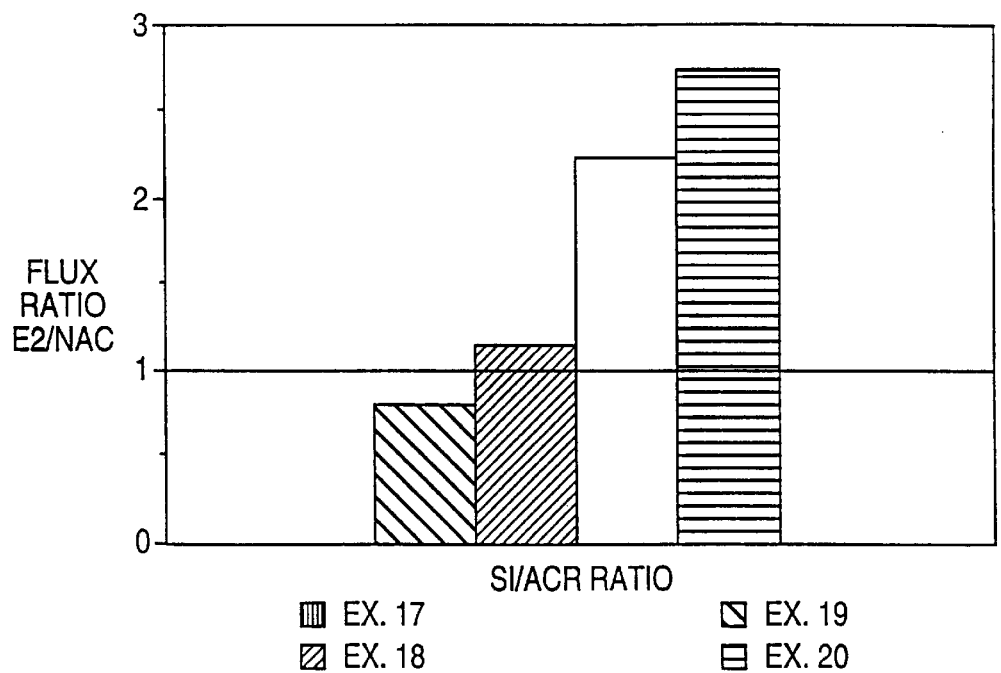
FIG. 9 is a graphical representation showing the ratio of average estradiol to norethindrone acetate flux (estradiol flux divided by norethindrone acetate flux) through cadaver skin in vitro for a multiple polymer transdermal adhesive system comprising various weight ratios of polyacrylate and polysiloxane.

Flux results for the compositions of Examples 17–20 are shown in FIG. 8. As shown in FIG. 8, the flux of both estradiol (E2) and norethindrone acetate (NAc) varied as the polysiloxane to polyacrylate polymer ratio was adjusted; estradiol flux gradually increased and then decreased with a maximum at about 15% acrylate, and the norethindrone acetate flux continuously decreased with increasing acrylate content as would be expected from the data of FIG. 7. A further effect of varying the polysiloxane/polyacrylate polymer ratio is exhibited by a plot of estradiol flux relative to norethindrone acetate flux (estradiol flux divided by norethindrone acetate flux) as shown in FIG. 9. By adjusting the silicone to acrylate polymer ratio, it was possible to modulate the relative delivery of two drugs (estradiol and norethindrone acetate) from the systems of this invention.

Examples 21–23

A pilocarpine-polymer mixture was prepared by combining 5.0 parts of pilocarpine base, 1.2 parts of lecithin, 0.8 parts of propylene glycol, 2.0 parts of oleic acid, 2.5 parts of silicone fluid (polydimethylsiloxane, Dow Corning 360 Medical Fluid, 100 cs), and 77.0 parts of polysiloxane (Dow Corning Silicone Adhesive BIO-PSA X7-3027), and mixing well in an appropriate container. Example 22 incorporated pilocarpine into a polyacrylate comprising National Starch Acrylic Adhesive, Duro-Tak 80-1196. Example 23 employed a blend of polysiloxane and polyacrylate in accordance with the principles of the invention. The resulting compositions had the ingredient concentrations on a "dry" basis, that is, after removal of volatile process solvents, given below in TABLE X.

TABLE X

Examples (% w/w)

| Ingredient | 21 | 22 | 23 |
|---|---|---|---|
| Polyacrylate | — | 82.0 | 41.0 |
| Polysiloxane | 77.0 | — | 41.0 |
| Silicone Fluid | 5.0 | — | — |
| Pilocarpine | 10.0 | 10.0 | 10.0 |
| Oleic acid | 4.0 | 4.0 | 4.0 |
| Propylene glycol | 1.6 | 1.6 | 1.6 |
| Lecithin | 2.4 | 2.4 | 2.4 |

Figure 10:
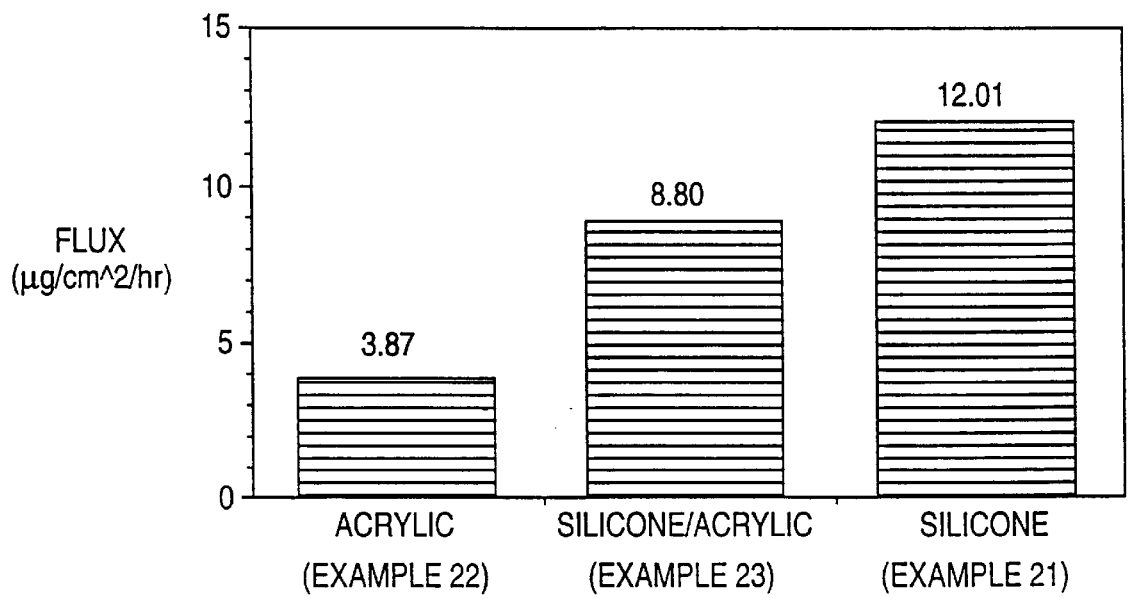
FIG. 10 is a graphical representation of steady-state flux of pilocarpine through cadaver skin in vitro from the drug delivery systems of the prior art, specifically single polymeric adhesives of silicone and acrylic, as compared to a multiple polymer transdermal adhesive system (polyacrylate/polysiloxane) of the present invention.

Pilocarpine flux in vitro from the systems of Examples 21, 22, and 23 is shown in FIG. 10. As seen in FIG. 10, the delivery rate from the system of this invention utilizing the multiple polymer adhesive (polyacrylate/polysiloxane) of Example 23, was intermediate of the delivery rates from single polymer compositions (Examples 21 and 22) which are not of this invention. In this embodiment of the invention, the combination of polyacrylate and polysiloxane polymers adjusted the delivery of rate of pilocarpine within the ranges established by single polymer compositions.

Examples 24–27

An albuterol-polymer mixture was prepared by combining 10.2 parts of albuterol base, 1.5 parts of lecithin, 1.0 part of propylene glycol, 4.1 parts of oleic acid, 2.6 parts of dipropylene glycol, 1.5 parts of butylene glycol, 1.5 parts of vitamin E acetate (tocoperyl acetate), 25.5 parts of polyacrylate (Duro-Tak 80-1196), 11.9 parts of polysiloxane A 9BIO-PSA X7-3122), 20.1 parts of polysiloxane B (BIO-PSA X7-3027), and 20.1 parts of isopropyl alcohol, and mixing well in an appropriate container. The resulting composition had the ingredient concentrations on a "dry" basis, that is, after removal of volatile process solvents, given below in Table XI.

The method of Example 24 was used with the appropriate amounts of starting materials to yield the compositions of Examples 25, 26, and 27.

TABLE XI

| | Examples (% w/w) | | | |
|---|---|---|---|---|
| Ingredient | 24 | 25 | 26 | 27 |
| Polysiloxane A | 14.0 | 13.8 | 14.0 | 14.0 |
| Polysiloxane B | 19.6 | 19.2 | 28.0 | 19.6 |
| Polyacrylate | 22.4 | 22.0 | 20.0 | 22.4 |
| Albuterol | 20.0 | 20.0 | 20.0 | 20.0 |
| Oleic acid | 8.0 | 8.0 | 8.0 | 8.0 |
| Propylene glycol | 2.0 | 2.0 | 2.0 | 2.0 |
| Dipropylene glycol | 5.0 | 5.0 | 5.0 | 5.0 |
| Butylene glycol | 3.0 | 3.0 | — | 3.0 |
| Vitamin E acetate | 3.0 | 3.0 | — | — |
| Vitamin E | — | 1.0 | — | — |
| Vitamin E linoleate | — | — | — | 3.0 |
| Lecithin | 3.0 | 3.0 | 3.0 | 3.0 |

Figure 11:
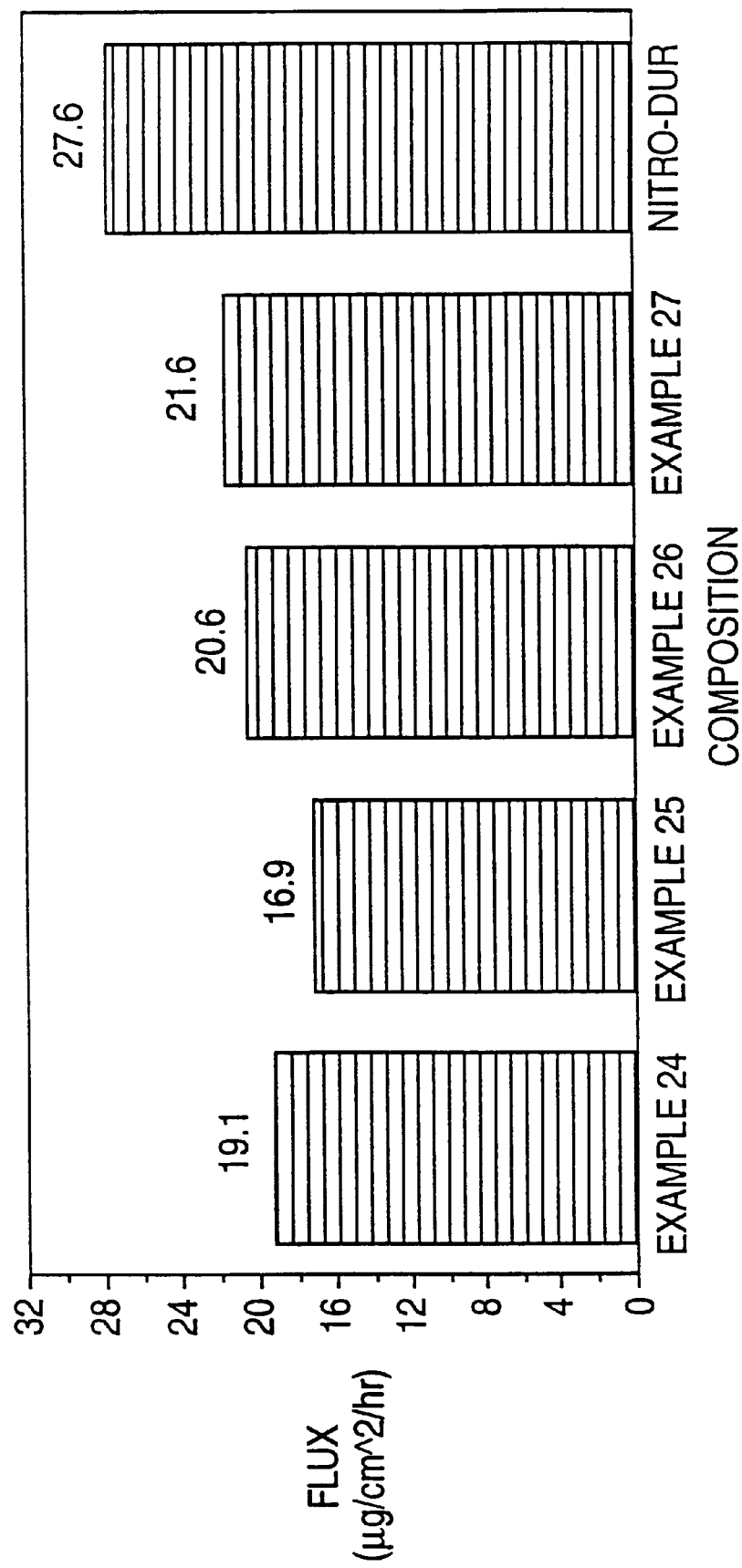
FIG. 11 is a graphical representation of steady-state albuterol and nitroglycerin flux through cadaver skin in vitro from multiple polymer transdermal adhesive systems (polyacrylate/polysiloxane) of the present invention (Examples 24–27), and Nitro-Dur®, respectively.

Albuterol flux results through human cadaver skin in vitro from the formulations of Examples 24, 25, 26, and 27, are summarized in FIG. 11; nitroglycerin flux from Nitro-Dur® through the same skin specimen is shown as a control. Flux values for the albuterol compositions of Example 24 to 27 ranged from about 17 $\mu$g/cm$^2$/hr to about 22 $\mu$g/cm$^2$/hr. The nitroglycerin flux value of about 28 $\mu$g/cm$^2$/hr was slightly higher than the literature delivery rate for this product (20 $\mu$g/cm$^2$/hr, based on Nitro-Dur® product label of 0.1 mg/hr from a 5 cm$^2$ system). In order to adjust for the apparent higher permeability of the skin specimen, albuterol flux results can be multiplied by an adjustment factor of 0.714 (20/28); this would result in flux values of about 12 $\mu$g/cm$^2$/hr to about 16 $\mu$g/cm$^2$/hr.

Therapeutic albuterol plasma concentrations are in the range of about 4 to 8 ng/mL, and are produced by delivery rates of about 115 to 230 $\mu$g/hr. The flux rates (12 to 16 $\mu$g/cm$^2$/hr) obtained from the compositions of this invention therefore would produce the necessary albuterol plasma levels (4 to 8 $\mu$g/mL) for the treatment of asthma from system sizes of about 10 to 20 cm$^2$.

Examples 28–29

Estradiol-polymer mixtures were prepared in accordance with the method of Example 7. Example 28 is illustrative of a multiple polymer adhesive system where polyacrylate is blended with polyisobutylene (Vistanex LM-LS-LC). The resulting compositions had the ingredient concentrations on a "dry" basis, that is, after removal of volatile process solvents, given below in TABLE XII.

TABLE XII

| | Examples (%, w/w) | |
|---|---|---|
| Ingredient | 28 | 29 |
| Polyacrylate | 45.0 | 45.0 |
| Polyisobutylene | 45.0 | — |
| Polysiloxane | — | 45.0 |
| Estradiol | 2.0 | 2.0 |
| Oleic acid | 5.0 | 5.0 |
| Lecithin | 3.0 | 3.0 |

Figure 12:
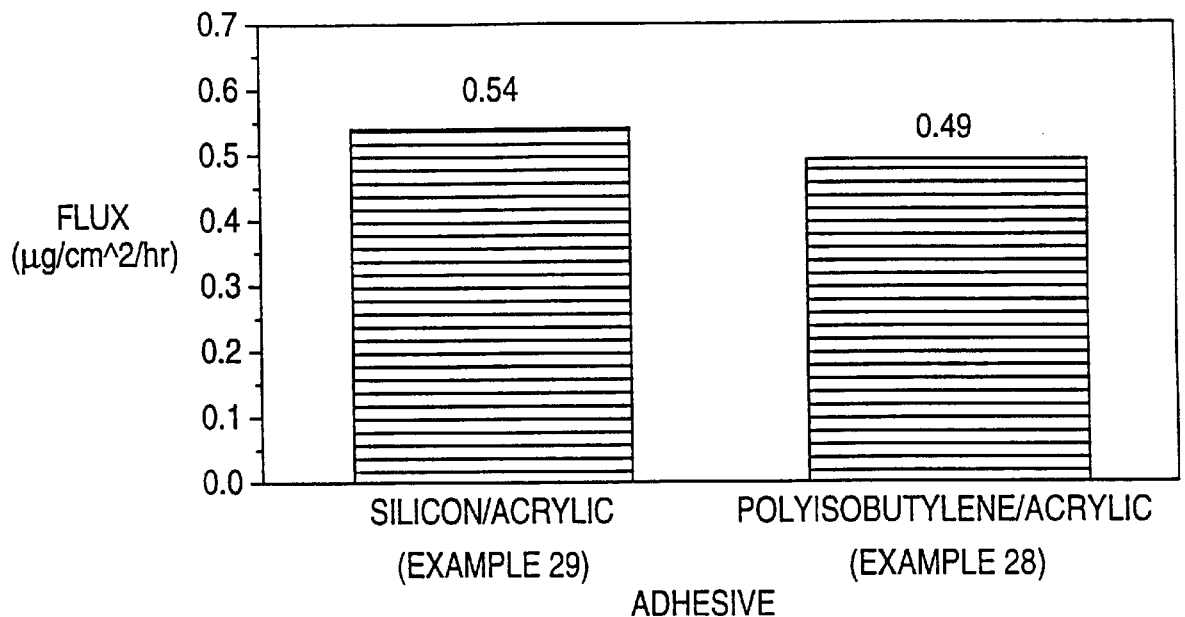
FIG. 12 is a graphical representation of steady-state estradiol flux through cadaver skin in vitro from two different multiple polymer transdermal adhesive systems: polyacrylate/polysiloxane and polyacrylate/polybutylene.

Estradiol flux in vitro from the systems of Examples 28 and 29 are shown in FIG. 12. As seen in FIG. 12, delivery from the multiple polymer adhesive system of Example 28 is comparable to delivery from Example 29.

Example 30

In addition to flux measurements, the apparent diffusion coefficient, D, was calculated from release data for nitroglycerin from matrices of Compositions I to VI (Example 6) into an infinite sink. The method of D. R. Paul, *Controlled Release Polymeric Formulations, ACS Symposium Series No. 33*, Chapter 1 (1976) was used wherein the initial concentration of nitroglycerin in the matrix, $C_0$, was determined (assuming a density of 1.0) and the relationship of the amount released, $M_t$, by a matrix of area, A, and the diffusion coefficient is defined by:

$$M_t/A = 2C_o(Dt/\pi)^{1/2}$$

Plotting, $M_t/A$ against $t^{1/2}$, results in a graph having a slope, m, defined by:

$$m = 2C_o(D/\pi)^{1/2}$$

The value of m can be ascertained by linear regression to get the slope of the best fit line. The diffusion coefficient is calculated as:

$$D = \pi(m/2C_o)^2$$

The results of these calculations for Compositions I to VI are shown below in Table XIII.

TABLE XIII

| Composition | $C_o$ (mg/cm$^3$) | m (mg/cm$^2$h$^{1/2}$) | D (cm$^2$/sec) | D(x10$^9$) |
|---|---|---|---|---|
| I | 241.0 | 0.8728 | 2.861 × 10$^{-9}$ | 2.86 |

TABLE XIII-continued

| Composition | $C_o$ (mg/cm$^3$) | m (mg/cm$^2$h$^{1/2}$) | D (cm$^2$/sec) | D(x10$^9$) |
|---|---|---|---|---|
| II | 233.3 | 0.9483 | 3.605 × 10$^{-8}$ | 36.05 |
| III | 231.3 | 1.0834 | 4.786 × 10$^{-8}$ | 47.86 |
| IV | 219.7 | 1.2502 | 7.065 × 10$^{-8}$ | 70.65 |
| V | 217.0 | 1.5920 | 1.174 × 10$^{-7}$ | 117.4 |
| VI | 215.0 | 2.4551 | 2.845 × 10$^{-7}$ | 284.5 |
| Nitro-Dur | 380.0 | 1.4680 | 3.256 × 10$^{-8}$ | 32.56 |

Figure 13:
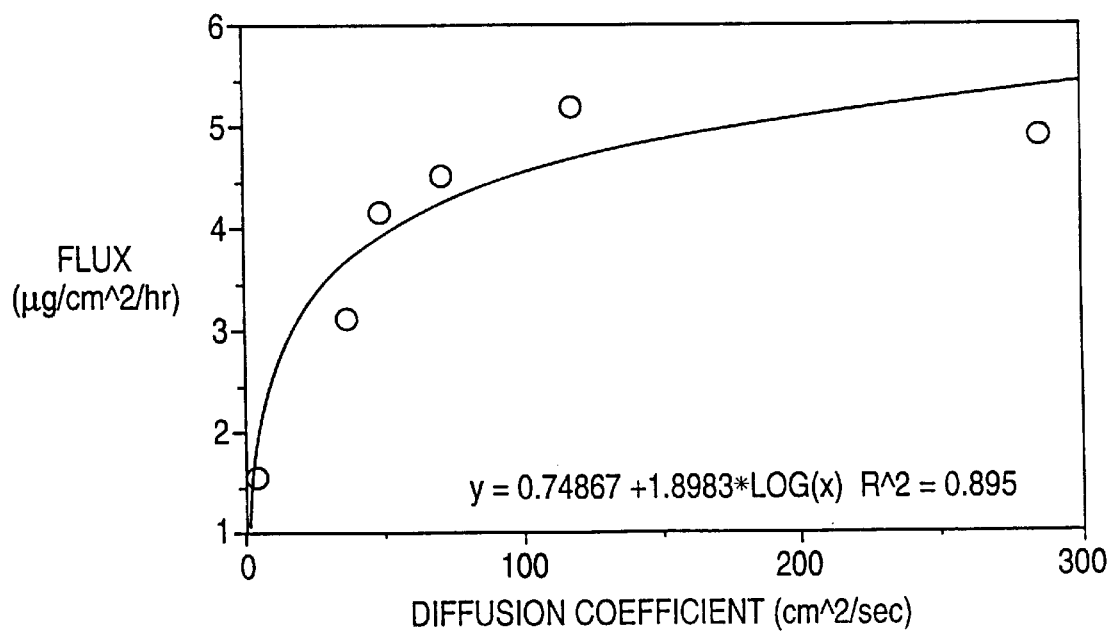
FIGS. 13 and 14 show the relationship of flux rate (J) plotted against apparent diffusion coefficient (D) and net solubility parameter (SP), respectively, for Compositions I–VI of Example 6. The net solubility parameter, $SP_{net}$, was calculated using a weighted average of the solubility parameters of the individual polymers comprising the matrix.
Figure 14:
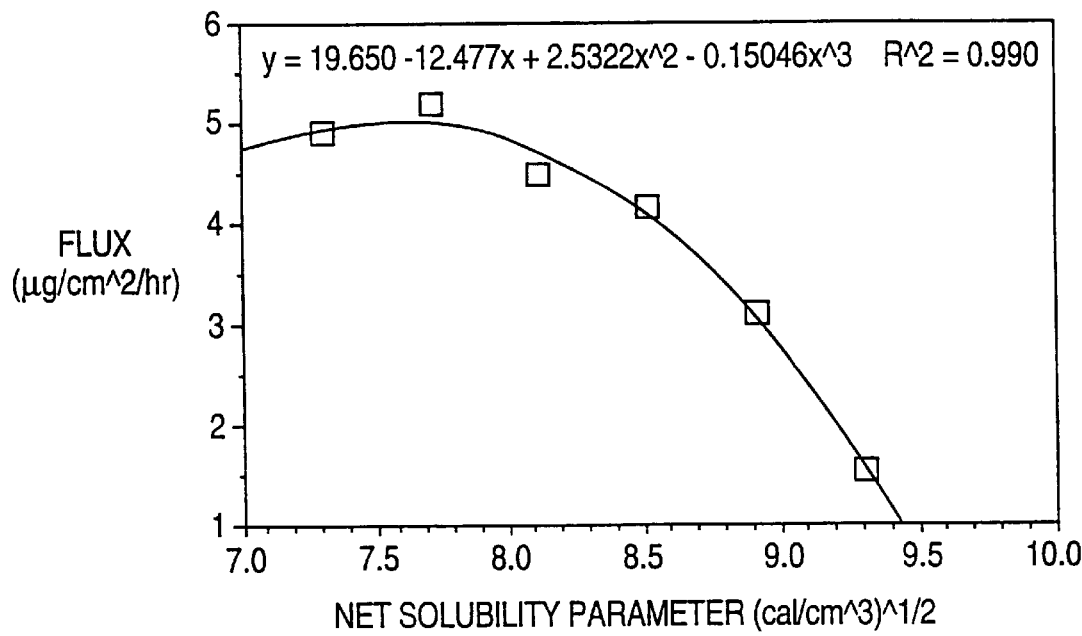

FIGS. 13 and 14 show the relationship of flux rate (J) plotted against apparent diffusion coefficient (D) and net solubility parameter (SP), respectively, for Compositions I–VI. The net solubility parameter, $SP_{net}$, was calculated using a weighted average of the solubility parameters of the individual polymers comprising the matrix:

$$SP_{net} = \Phi_{ps} SP_{ps} + \Phi_{pa} SP_{pa},$$

where $\Phi_{ps}$ is the weight percentage of polysiloxane and $SP_{ps}$ is the solubility parameter of polysiloxane. The subscript "pa" refers to the polyacrylate. FIG. 15 is a plot of diffusion coefficient versus net solubility parameter.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A dermal composition, comprising a blend of:
   (a) a polyacrylate and a second polymer selected from the group consisting of a polysiloxane and a hydrocarbon polymer; and
   (b) a therapeutically effective amount of a drug for transdermal administration,
   wherein the composition is a pressure-sensitive adhesive and the polyacrylate and the second polymer modulates the permeation rate of the drug through the dermis, and wherein the composition excludes a polyethylene/vinyl acetate copolymer.

2. The composition of claim 1, which further comprises a hydrophilic filler.

3. The composition of claim 2, wherein the hydrophilic filler includes aluminum silicate clay.

4. The composition of claim 1, wherein the drug is a steroid.

5. The composition of claim 4, wherein the steroid is an estrogen selected from the group consisting of, estropipate, 17β-estradiol, equilin, mestranol, estrone, estriol, ethinyl estradiol, and diethylstilbestrol.

6. The composition of claim 4, wherein the steroid is a progestational agent.

7. The composition of claim 6, wherein the progestational agent is selected from the group consisting of progesterone, 19-norprogesterone, norethindrone, norethindrone acetate, melengestrol, chloromadinone, ethisterone, medroxyprogesterone acetate, hydroxyprogesterone caproate, ethynodiol diacetate, norethynodrel, 17α-hydroxyprogesterone, dydrogesterone, dimethisterone, ethinylestrenol, demegestone, promegestone, and megestrol acetate.

8. The composition of claim 1, wherein the drug is a cardioactive drug.

9. The composition of claim 8, wherein said cardioactive agent is selected from the group consisting of nitroglycerin, isosorbide dinitrate, isosorbide mononitrate, quinidine sulfate, procainamide, benzydroflumethiazide, bendroflumethiazide, chlorothiazide, nifedipine, nicardipine, verapamil, diltiazem, timolol, propranolol, captopril, clonidine and prazosin.

10. The composition of claim 1, wherein said composition is a reservoir device having an adhesive portion comprised of said blend.

11. The composition of claim 5, wherein the estrogen is 17β-estradiol and the 17β-estradiol is present in the composition in an amount of from about 1% to about 5% by weight.

12. The composition of claim 7, wherein the progestational agent is norethindrone acetate and the norethindrone acetate is present in the composition in an amount of from about 1% to about 5% by weight.

13. The composition of claim 1, wherein the drug is albuterol and the albuterol is present in the composition in an amount of up to about 30% by weight.

14. The composition of claim 9, wherein the cardioactive agent is nitroglycerin and the nitroglycerin is present in the composition in an amount of less than about 25% by weight.

15. The composition of claim 1, wherein the drug is pilocarpine and the pilocarpine is present in the composition in an amount of less than about 30% by weight.

16. The composition of claim 1, wherein the drug is a tranquilizer.

17. The composition of claim 16, wherein the tranquilizer is selected from the group consisting of alprazolam, chlordiazepoxide, clorazeptate, halazepam, oxazepam, prazepam, clonazepam, flurazepam, triazolam, lorazepam and diazepam.

18. The composition of claim 17, wherein the tranquilizer is alprazolam.

19. The composition of claim 1, wherein the drug is an antipsychotic.

20. The composition of claim 19, wherein the antipsychotic is selected from the group consisting of thiopropazate, chlorpromazine, triflupromazine, mesoridazine, piperacetazine, thioridazine, acetophenazine, fluphenazine, perphenazine, trifluoperazine, chlorprathixene, thiothixene, haloperidol, bromperidol, loxapine and molindone.

21. The composition of claim 20, wherein the antipsychotic is haloperidol.

22. The composition of claim 1, wherein the drug is an anesthetic.

23. The composition of claim 22, wherein the anesthetic is selected from the group consisting of lidocaine, tetracaine, dyclonine, dibucaine, cocaine, procaine, mepivacaine, bupivacaine, etidocaine, prilocaine and benzocaine.

24. The composition of claim 23, wherein the anesthetic is lidocaine.

25. The composition of claim 1, wherein the drug is an analgesic.

26. The composition of claim 25, wherein the analgesic is selected from the group consisting of fentanyl, buprenorphine and codeine.

27. The composition of claim 1, wherein the drug has an action on the central nervous system.

28. The composition of claim 27, wherein the drug is nicotine.

29. The composition of claim 1, comprising a mixture of at least two drugs.

30. The composition of claim 29, comprising a mixture of a progestational agent and an estrogen.

31. The composition of claim 30, wherein said progestational agent is selected from the group consisting of progesterone, 19-norprogesterone, norethindrone, norethindrone acetate, melengestrol, chloromadinone, ethisterone, medroxyprogesterone acetate, hydroxyprogesterone caproate, ethynodiol diacetate, norethynodrel, 17α-hydroxyprogesterone, dydrogesterone, dimethisterone, ethinylestrenol, norgestrel, demegestone, promegestone, and megestrol acetate.

32. The composition of claim 31, wherein said progestational agent is norethindrone acetate.

33. The composition of claim 30, wherein said estrogen is selected from the group consisting of conjugated estrogens, esterified estrogens, estropipate, 17β-estradiol, equilin, mestranol, estrone, estriol, ethinyl estradiol, and diethylstilbestrol.

34. The composition of claim 33, wherein said estrogen is 17β-estradiol.

35. The composition of claim 1, wherein said composition achieves an increased permeation rate of the drug through the dermis of a subject relative to the permeation rate achieved by a composition comprising one of said polyacrylate or said second polymer as the sole polymer.

36. The composition of claim 1, wherein said composition achieves a decreased permeation rate of the drug through the dermis of a subject relative to the permeation rate achieved by a composition comprising said one of said polyacrylate or said second polymer as the sole polymer.

37. The composition of claim 1, further comprising one or more additives selected from the group consisting of one or more enhancers, a filler, a co-solvent and an excipient.

38. The composition of claim 1, wherein the polymers of the blend consist essentially of the polyacrylate and second polymer.

39. The composition of claim 1, wherein the polymers of the blend consist essentially of the polysiloxane and the polyacrylate.

40. The composition of claim 39, wherein the polyacrylate is present in an amount ranging from about 2% to about 96% by weight of the composition and the polysiloxane is present in an amount ranging from about 98% to about 4% by weight of the composition.

41. The composition of claim 39, which comprises based on the weight of the composition, about 0.3 to about 50% by weight of albuterol, about 14 to about 97% by weight of polysiloxane, about 2 to about 85% by weight of polyacrylate, 0 up to about 20% by weight of enhancers, and about 0 up to about 30% by weight of cosolvents.

42. The composition of claim 1, wherein the blend includes additional polymers.

43. A pressure-sensitive adhesive composition for dermal administration of a drug comprising a blend of:
(a) two polymers consisting essentially of about 2% to about 96% by weight of a polyacrylate and about 98% to about 4% by weight of a polysiloxane, the two polymers being in an amount of about 99% to about 50% by weight of said composition;
(b) a drug in the amount of about 0.3% to about 50% by weight of said composition;
(c) an effective amount of a co-solvent for the drug, said amount being up to about 30% by weight of said composition; and
(d) an effective amount of an enhancer, said amount being up to about 20% by weight of said composition.

44. The composition of claim 43, further comprising fillers and excipients in an amount of about 1% to about 15% by weight of the dermal adhesive composition.

45. A process for transdermally administering to a mammal a therapeutically effective amount of a drug, comprising the steps of applying a composition for transdermal administration of the drug to the skin of said mammal, and maintaining said composition in contact with said skin until said effective amount of said preselected drug is transdermally administered, wherein said composition comprises a blend of
(a) two or more polymers which includes a polyacrylate and one or more of a polysiloxane, polyvinylchloride, polyvinylidene chloride, polychloroprene, polyacrylonitrile, nylon-6,6, epoxy resin, a copolymer of polybutadiene/acrylonitrile and a hydrocarbon polymer, said at least two polymers have corresponding solubility parameters and are blended in a proportion, resulting in a net solubility parameter of the blend; and
(b) said preselected drug, wherein the composition is a pressure-sensitive adhesive wherein the net solubility parameter of the blend determines the solubility of the preselected drug in the blend, and wherein the composition excludes a polyethylene/vinyl acetate copolymer.

46. A composition as claimed in claim 1, wherein the polyacrylate and the second polymer are pressure-sensitive adhesives.

47. The dermal composition as claimed in claim 38, wherein the polymers of the blend consist essentially of the polyacrylate and the hydrocarbon polymer.

48. The composition as claimed in claim 47, wherein the hydrocarbon polymer is selected from the group consisting of polyethylene, polystyrene, polyisobutylene, polybutadiene and the copolymer of polyethylene/butylene.

49. The composition as claimed in claim 48, wherein the hydrocarbon polymer is polyisobutylene.

50. A dermal composition, comprising a blend of:
(a) a polyacrylate having a first solubility parameter and a second polymer selected from the group consisting of polysiloxane and hydrocarbon polymers having a second solubility parameter, wherein the first and second solubility parameters are different from one another by an increment of at least 4 $(J/cm^3)^{1/2}$; and
(b) a therapeutically effective amount of a drug for transdermal administration,
wherein the composition is a pressure-sensitive adhesive and the polyacrylate and the second polymer modulates the permeation rate of the drug through the dermis, and wherein the composition excludes a polyethylene/vinyl acetate copolymer.

51. A composition for dermal administration of a drug, comprising a blend of:
(a) a polyacrylate and a second polymer selected from the group consisting of polyvinylchloride, polyvinylidene chloride, polychloroprene, polyacrylonitrile, nylon-6,6, epoxy resin, and a copolymer of polybutadiene/acrylonitrile; and
(b) a therapeutically effective amount of a drug for transdermal administration,
wherein the composition is a pressure-sensitive adhesive and the polyacrylate and the second polymer modulates the permeation rate of the drug through the dermis, and wherein the composition excludes a polyethylene/vinyl acetate copolymer.

52. The composition of claim 40, wherein the composition further comprises dipropylene glycol, and wherein the drug is estradiol.

53. The composition of claim 52, wherein the drug is 17β-estradiol.

54. The composition of claim 40, wherein the composition further comprises dipropylene glycol and oleic acid, and wherein the drug includes a further drug, wherein said drug and further drug selected from the group of an estrogen and a progestational agent.

55. The composition of claim 54, wherein the estrogen is 17β-estradiol.

56. The composition of claim 55, wherein the progestational agent is one or more norethindrone and norethindrone acetate.

57. A composition according to claim 1, wherein the composition consists essentially of the polyacrylate, the second polymer and one or more drugs.

58. A process according to claim 45, wherein the one or more polymers includes polysiloxane.

59. A process according to claim 45, wherein the composition consists essentially of the polyacrylate, the second polymer and one or more drugs.

60. A proces according to claim 45, wherein the second polymer includes the hydrocarbon polymer which is selected from the group consisting of polyethylene, polystyrene, polyisobutylene, polybutadiene, and polyethylene/butylene, and mixtures thereof.

61. The composition of claim 1, wherein the drug is an androgenic steroid.

62. The composition of claim 1, wherein the drug is an Parkinsonian agent.

63. The composition of claim 62, wherein the Parkinsonian agent is selegiline (deprenyl).

64. The composition of claim 1, wherein the drug is an anti-inflamatory.

65. The composition of claim 64, wherein the anti-inflammatory agent is selected from the group consisting of fenoprofen, flurbiprofen, ibuprofen, ketoprofen, naproxen, peroxicam, fludrocortisone, betamethasone, flucinolone, flurandrenolide, prednisolone and prednisone.

66. The composition of claim 1, wherein the drug is an anorectic.

67. The composition of claim 66, wherein the anorectic is selected from the group consisting of fenfluramine, mazindol and phentermine.

68. The composition of claim 1, wherein the drug is selected from the group consisting of misoprostol, baclofen, scopolamine, tetracycline, albuterol, alprazolam, and haloperidol.

69. The composition of claim 29, wherein the first drug is an anesthetic and the second drug is elected from the group consisting of analgesics, anesthetics and anti-inflammatories.

70. The composition of claim 1, which further comprises:
   a backing layer which is in contact with a first surface of the dermal composition; and
   a release layer which is in contact with and which releasably covers the opposite surface of the dermal composition.

71. The composition of claim 50, which further comprises:
   a backing layer which is in contact with a first surface of the dermal composition; and
   a release layer which is in contact with and which releasably covers the opposite surface of the dermal composition.

72. The composition of claim 51, which further comprises:
   a backing layer which is in contact with a first surface of the dermal composition; and
   a release layer which is in contact with and which releasably covers the opposite surface of the dermal composition.

73. A process according to claim 45, wherein before administration, the composition is positioned between a backing layer which is in contact with a first surface of the composition, and a release layer which is in contact with and which releasably covers the opposite surface of the composition.

74. The composition of claim 37, wherein the drug is for Parkinson's disease, the co-solvent is selected from the group consisting of propylene glycol, saturated fatty acids and unsaturated fatty acids, and the one or more enhancers are selected from the group consisting of a polyhydric alcohol, a polar solvent, a higher molecular weight aliphatic surfactant and oleic acid.

75. The composition of claim 74, wherein the drug for Parkinson's disease is levodopa, and the enhancer is propylene glycol and lauryl sulfate.

* * * * *